United States Patent
Cook et al.

(10) Patent No.: US 9,625,465 B2
(45) Date of Patent: Apr. 18, 2017

(54) CLINICAL DIAGNOSTIC SYSTEMS

(71) Applicant: Wellstat Diagnostics, LLC, Gaithersburg, MD (US)

(72) Inventors: Richard Alan Cook, Derwood, MD (US); Sang Cho, Rockville, MD (US); Charles Quentin Davis, Frederick, MD (US); Kevin E Dorsey, Germantown, MD (US); Jason Charles Harley, Gaithersburg, MD (US); Jonathan Leland, Gaithersburg, MD (US); Rober Krikor Matikyan, Potomac, MD (US); Sjef Otten, Gaithersburg, MD (US); Jeffrey Howard Peterman, Silver Spring, MD (US); Brian B Thomas, Frederick, MD (US)

(73) Assignee: DEFINED DIAGNOSTICS, LLC, Chevy Chase, MD (US)

( * ) Notice: Subject to any disclaimer, the term of this patent is extended or adjusted under 35 U.S.C. 154(b) by 0 days.

(21) Appl. No.: 14/401,278

(22) PCT Filed: May 15, 2013

(86) PCT No.: PCT/US2013/041255
§ 371 (c)(1),
(2) Date: Nov. 14, 2014

(87) PCT Pub. No.: WO2013/173525
PCT Pub. Date: Nov. 21, 2013

(65) Prior Publication Data
US 2015/0132861 A1    May 14, 2015

Related U.S. Application Data

(63) Continuation-in-part of application No. PCT/US2013/041252, filed on May 15, 2013, and a
(Continued)

(51) Int. Cl.
*G01N 21/76* (2006.01)
*G01N 33/58* (2006.01)
(Continued)

(52) U.S. Cl.
CPC ...... *G01N 33/582* (2013.01); *B01L 3/502715* (2013.01); *G01N 33/536* (2013.01);
(Continued)

(58) Field of Classification Search
CPC ...... G01N 33/50; G01N 21/66; F04B 49/065; F04B 49/106; H05B 1/025
See application file for complete search history.

(56) References Cited

U.S. PATENT DOCUMENTS 3,705,100 A    12/1972  Blatt et al.
4,212,742 A     7/1980  Solomon et al.
(Continued)

FOREIGN PATENT DOCUMENTS

EP    486059      1/1997
EP    0962773    12/1999
(Continued)

OTHER PUBLICATIONS

Ascoli, et al., "Drug Binding to Human Serum Albumin: Abridged Review of Results Obtained with High-Performance Liquid Chromatography and Circular Dichroism", Chirality, vol. 18:667-679 (2006).
(Continued)

*Primary Examiner* — Dennis M White

(57) ABSTRACT

A diagnostic system is provided herein that includes an instrument comprising an electrochemiluminescence (ECL) detector, and a cartridge configured to fit within a portion of the instrument, wherein the cartridge includes at least one reagent including an ECL label and a blood collection holder. Also provided herein is a system that includes a
(Continued)

diagnostic instrument, which includes a pump, an ECL detector, an incubator, a magnet, and an output device, and a cartridge configured to fit within a portion of the diagnostic instrument, a sample holder configured to fit within the cartridge, and a closed fluidic loop between the diagnostic instrument and the cartridge when the cartridge is fit within a portion of the diagnostic instrument, wherein the cartridge is configured to accept a sample from the sample holder and place the sample in fluidic communication with the diagnostic instrument via the closed fluidic loop.

25 Claims, 21 Drawing Sheets

Related U.S. Application Data continuation-in-part of application No. 13/844,527, filed on Mar. 15, 2013, now Pat. No. 9,075,042, and a continuation-in-part of application No. 13/844,450, filed on Mar. 15, 2013, now Pat. No. 9,081,001, and a continuation-in-part of application No. PCT/US2012/067041, filed on Nov. 29, 2012.

(60) Provisional application No. 61/647,272, filed on May 15, 2012.

(51) Int. Cl.
 *G01N 33/536* (2006.01)
 *G01N 33/543* (2006.01)
 *B01L 3/00* (2006.01)

(52) U.S. Cl.
 CPC ........... *G01N 33/543* (2013.01); *G01N 33/58* (2013.01); *B01L 2200/10* (2013.01); *B01L 2300/0645* (2013.01); *B01L 2300/0672* (2013.01); *B01L 2300/0681* (2013.01); *B01L 2300/0816* (2013.01); *Y10T 436/147777* (2015.01); *Y10T 436/25* (2015.01); *Y10T 436/2575* (2015.01)

(56) References Cited

U.S. PATENT DOCUMENTS

| | | |
|---|---|---|
| 4,225,410 A | 9/1980 | Pace |
| 4,228,015 A | 10/1980 | De Vries et al. |
| 4,301,412 A | 11/1981 | Hill et al. |
| 4,301,414 A | 11/1981 | Hill et al. |
| 4,336,121 A | 6/1982 | Enzer et al. |
| 4,381,775 A | 5/1983 | Nose et al. |
| 4,397,725 A | 8/1983 | Enzer et al. |
| 4,436,610 A | 3/1984 | Enzer et al. |
| 4,540,492 A | 9/1985 | Kessler |
| 4,548,498 A | 10/1985 | Folestad et al. |
| 4,631,130 A | 12/1986 | Watanabe |
| 4,675,300 A | 6/1987 | Zare et al. |
| 4,735,718 A | 4/1988 | Peters |
| 4,735,776 A | 4/1988 | Yamamoto et al. |
| 4,762,594 A | 8/1988 | Guruswamy |
| 4,786,394 A | 11/1988 | Enzer et al. |
| 4,799,393 A | 1/1989 | Uffenheimer |
| 4,820,129 A | 4/1989 | Magnussen, Jr. |
| 4,833,087 A | 5/1989 | Hinckley |
| 4,835,477 A | 5/1989 | Polaschegg et al. |
| 4,887,458 A | 12/1989 | Baker et al. |
| 4,929,426 A | 5/1990 | Bodai et al. |
| 4,965,049 A | 10/1990 | Lillig et al. |
| 5,023,054 A | 6/1991 | Sato et al. |
| 5,061,445 A | 10/1991 | Zoski et al. |
| 5,068,088 A | 11/1991 | Hall et al. |
| 5,074,977 A | 12/1991 | Cheung et al. |
| 5,093,268 A | 3/1992 | Leventis et al. |
| 5,096,582 A | 3/1992 | Lombardi et al. |
| 5,130,254 A | 7/1992 | Collier et al. |
| 5,139,328 A | 8/1992 | Baker et al. |
| 5,139,685 A | 8/1992 | de Castro et al. |
| 5,143,084 A | 9/1992 | Macemon et al. |
| 5,147,806 A | 9/1992 | Kamin et al. |
| 5,155,039 A | 10/1992 | Chrisope et al. |
| 5,208,163 A | 5/1993 | Charlton et al. |
| 5,223,219 A | 6/1993 | Subramanian et al. |
| 5,223,718 A | 6/1993 | Taboada |
| 5,238,808 A | 8/1993 | Bard et al. |
| 5,247,243 A | 9/1993 | Hall et al. |
| 5,279,797 A | 1/1994 | Burns et al. |
| 5,288,646 A | 2/1994 | Lundsgaard et al. |
| 5,296,191 A | 3/1994 | Hall et al. |
| 5,298,224 A | 3/1994 | Plum |
| 5,302,348 A | 4/1994 | Cusack et al. |
| 5,310,687 A | 5/1994 | Bard et al. |
| 5,316,730 A | 5/1994 | Blake et al. |
| 5,372,946 A | 12/1994 | Cusack et al. |
| 5,399,486 A | 3/1995 | Cathey et al. |
| 5,405,510 A | 4/1995 | Betts et al. |
| 5,416,026 A | 5/1995 | Davis |
| 5,453,356 A | 9/1995 | Bard et al. |
| 5,466,416 A | 11/1995 | Ghaed et al. |
| 5,487,870 A | 1/1996 | McKinney et al. |
| 5,500,187 A | 3/1996 | Deoms et al. |
| 5,504,011 A | 4/1996 | Gavin et al. |
| 5,506,142 A | 4/1996 | Mahaffey et al. |
| 5,522,255 A | 6/1996 | Neel et al. |
| 5,525,518 A | 6/1996 | Lundsgaard et al. |
| 5,527,710 A | 6/1996 | Nacamulli et al. |
| 5,534,226 A | 7/1996 | Gavin et al. |
| 5,543,112 A | 8/1996 | Ghead et al. |
| 5,558,838 A | 9/1996 | Uffenheimer |
| 5,567,869 A | 10/1996 | Hauch et al. |
| 5,575,977 A | 11/1996 | McKinney et al. |
| 5,591,403 A | 1/1997 | Gavin et al. |
| 5,591,581 A | 1/1997 | Massey et al. |
| 5,593,638 A | 1/1997 | Davis |
| 5,597,910 A | 1/1997 | Gudibande et al. |
| 5,599,447 A | 2/1997 | Pearl et al. |
| 5,601,727 A | 2/1997 | Bormann et al. |
| 5,602,037 A | 2/1997 | Ostgaard et al. |
| 5,610,075 A | 3/1997 | Stahl-Rees |
| 5,624,637 A | 4/1997 | Ghaed et al. |
| 5,627,041 A | 5/1997 | Shartle |
| 5,629,209 A | 5/1997 | Braun, Sr. et al. |
| 5,635,347 A | 6/1997 | Link et al. |
| 5,641,623 A | 6/1997 | Martin |
| 5,643,713 A | 7/1997 | Liang et al. |
| 5,653,243 A | 8/1997 | Lauks et al. |
| 5,660,993 A | 8/1997 | Cathey et al. |
| 5,665,238 A | 9/1997 | Whitson et al. |
| 5,665,315 A | 9/1997 | Robert et al. |
| 5,666,967 A | 9/1997 | Lauks et al. |
| 5,679,519 A | 10/1997 | Oprandy et al. |
| 5,686,244 A | 11/1997 | Gudibande et al. |
| 5,698,406 A | 12/1997 | Cathey et al. |
| 5,700,427 A | 12/1997 | Ghaed et al. |
| 5,705,402 A | 1/1998 | Leland et al. |
| 5,714,089 A | 2/1998 | Bard et al. |
| 5,716,781 A | 2/1998 | Massey et al. |
| 5,720,922 A | 2/1998 | Ghaed et al. |
| 5,731,147 A | 3/1998 | Bard et al. |
| 5,736,404 A | 4/1998 | Yassinzadeh et al. |
| 5,743,861 A | 4/1998 | Columbus et al. |
| 5,744,367 A | 4/1998 | Talley et al. |
| 5,746,974 A | 5/1998 | Massey et al. |
| 5,747,666 A | 5/1998 | Willis |
| 5,770,459 A | 6/1998 | Massey et al. |
| 5,779,650 A | 7/1998 | Lauks et al. |
| 5,779,976 A | 7/1998 | Leland et al. |
| 5,795,543 A | 8/1998 | Poto et al. |
| 5,798,083 A | 8/1998 | Massey et al. |
| 5,800,781 A | 9/1998 | Gavin et al. |
| 5,804,400 A | 9/1998 | Martin et al. |
| 5,821,399 A | 10/1998 | Zelin |
| 5,827,481 A | 10/1998 | Bente et al. |

(56) References Cited

U.S. PATENT DOCUMENTS

| | | |
|---|---|---|
| 5,846,485 A | 12/1998 | Leland et al. |
| 5,851,488 A | 12/1998 | Saul et al. |
| RE36,054 E | 1/1999 | Blake et al. |
| 5,858,676 A | 1/1999 | Yang et al. |
| 5,882,602 A | 3/1999 | Savage et al. |
| 5,885,533 A | 3/1999 | Savage et al. |
| 5,888,826 A | 3/1999 | Ostgaard et al. |
| 5,912,134 A | 6/1999 | Shartle |
| 5,914,042 A | 6/1999 | Ball et al. |
| 5,919,711 A | 7/1999 | Boyd et al. |
| 5,922,210 A | 7/1999 | Brody et al. |
| 5,935,779 A | 8/1999 | Massey et al. |
| 5,945,344 A | 8/1999 | Hayes et al. |
| 5,962,218 A | 10/1999 | Leland et al. |
| 5,968,329 A | 10/1999 | Anderson et al. |
| 5,980,830 A | 11/1999 | Savage et al. |
| 5,981,294 A | 11/1999 | Blatt et al. |
| 5,983,734 A | 11/1999 | Mathur et al. |
| 6,016,712 A | 1/2000 | Warden et al. |
| 6,048,687 A | 4/2000 | Kenten et al. |
| 6,057,151 A | 5/2000 | Greenwood et al. |
| 6,069,014 A | 5/2000 | Schrier et al. |
| 6,078,782 A | 6/2000 | Leland et al. |
| 6,082,185 A | 7/2000 | Saaski |
| 6,087,476 A | 7/2000 | Kenten et al. |
| 6,096,500 A | 8/2000 | Oprandy et al. |
| 6,099,760 A | 8/2000 | Jameison et al. |
| 6,112,888 A | 9/2000 | Sauro et al. |
| 6,120,986 A | 9/2000 | Martin |
| 6,132,648 A | 10/2000 | Zhang et al. |
| 6,132,955 A | 10/2000 | Talley et al. |
| 6,140,138 A | 10/2000 | Bard et al. |
| 6,146,838 A | 11/2000 | Williams et al. |
| 6,165,708 A | 12/2000 | Liang et al. |
| 6,165,729 A | 12/2000 | Leland et al. |
| 6,174,709 B1 | 1/2001 | Kenten et al. |
| 6,187,267 B1 | 2/2001 | Taylor et al. |
| 6,193,864 B1 | 2/2001 | Leader et al. |
| 6,200,531 B1 | 3/2001 | Liljestrand et al. |
| 6,214,552 B1 | 4/2001 | Heroux et al. |
| 6,217,744 B1 | 4/2001 | Crosby |
| 6,271,041 B1 | 8/2001 | Leland et al. |
| 6,274,087 B1 | 8/2001 | Preston et al. |
| 6,312,591 B1 | 11/2001 | Vassarotti et al. |
| 6,312,896 B1 | 11/2001 | Heroux et al. |
| 6,316,180 B1 | 11/2001 | Martin |
| 6,316,607 B1 | 11/2001 | Massey et al. |
| 6,319,670 B1 | 11/2001 | Sigal et al. |
| 6,319,719 B1 | 11/2001 | Bhullar et al. |
| 6,325,973 B1 | 12/2001 | Leland et al. |
| 6,379,969 B1 | 4/2002 | Mauze et al. |
| 6,387,290 B1 | 5/2002 | Brody et al. |
| 6,391,541 B1 | 5/2002 | Petersen et al. |
| 6,398,956 B1 | 6/2002 | Coville et al. |
| 6,403,384 B1 | 6/2002 | Lea |
| 6,406,672 B1 | 6/2002 | Buhllar et al. |
| 6,432,720 B2 | 8/2002 | Chow |
| 6,438,498 B1 | 8/2002 | Opalsky et al. |
| 6,440,725 B1 | 8/2002 | Pourahmadi et al. |
| 6,448,091 B1 | 9/2002 | Massey et al. |
| 6,451,225 B1 | 9/2002 | Leland et al. |
| 6,468,741 B1 | 10/2002 | Massey et al. |
| 6,475,372 B1 | 11/2002 | Ohara et al. |
| 6,479,233 B1 | 11/2002 | Bard et al. |
| 6,488,896 B2 | 12/2002 | Weigl et al. |
| 6,495,104 B1 | 12/2002 | Unno et al. |
| 6,517,777 B2 | 2/2003 | Liljestrand et al. |
| 6,524,513 B1 | 2/2003 | Pearl et al. |
| 6,524,865 B1 | 2/2003 | Martin et al. |
| 6,534,137 B1 | 3/2003 | Vadhar |
| 6,537,501 B1 | 3/2003 | Holl et al. |
| 6,554,788 B1 | 4/2003 | Hunley et al. |
| 6,559,096 B1 | 5/2003 | Smith et al. |
| 6,613,280 B2 | 9/2003 | Myrick et al. |
| 6,613,286 B2 | 9/2003 | Braunn, Sr. et al. |
| 6,613,583 B1 | 9/2003 | Richter et al. |
| 6,635,418 B2 | 10/2003 | Heroux et al. |
| 6,656,428 B1 | 12/2003 | Clark et al. |
| 6,664,104 B2 | 12/2003 | Pourahmadi et al. |
| 6,676,902 B2 | 1/2004 | Baugh et al. |
| 6,699,718 B1 | 3/2004 | Bruegger |
| 6,702,986 B1 | 3/2004 | Leland et al. |
| 6,740,240 B2 | 5/2004 | Coville et al. |
| 6,748,332 B2 | 6/2004 | Chen |
| 6,750,053 B1 | 6/2004 | Widrig Opalsky et al. |
| D494,589 S | 8/2004 | Liljestrand et al. |
| 6,776,965 B2 | 8/2004 | Wyzgol et al. |
| 6,783,736 B1 | 8/2004 | Taylor et al. |
| 6,794,877 B2 | 9/2004 | Blomberg et al. |
| 6,808,939 B2 | 10/2004 | Sigal et al. |
| D499,035 S | 11/2004 | Cook et al. |
| 6,818,185 B1 | 11/2004 | Petersen et al. |
| 6,824,663 B1 | 11/2004 | Boone |
| 6,831,733 B2 | 12/2004 | Pettersson et al. |
| 6,846,629 B2 | 1/2005 | Sigal et al. |
| 6,852,284 B1 | 2/2005 | Holl et al. |
| 6,852,502 B1 | 2/2005 | Martin |
| 6,861,259 B2 | 3/2005 | Columbus |
| 6,866,823 B2 | 3/2005 | Wardlaw |
| 6,869,570 B2 | 3/2005 | Wardlaw |
| 6,878,540 B2 | 4/2005 | Pourahmadi et al. |
| 6,880,384 B2 | 4/2005 | Hvidtfeldt et al. |
| 6,881,536 B1 | 4/2005 | Shah et al. |
| 6,881,541 B2 | 4/2005 | Petersen et al. |
| 6,881,589 B1 | 4/2005 | Leland et al. |
| 6,887,693 B2 | 5/2005 | McMillan et al. |
| 6,893,879 B2 | 5/2005 | Petersen et al. |
| 6,919,173 B2 | 7/2005 | Tsionsky et al. |
| 6,926,834 B2 | 8/2005 | Coville et al. |
| 6,929,953 B1 | 8/2005 | Wardlaw |
| 6,949,377 B2 | 9/2005 | Ho |
| 6,969,450 B2 | 11/2005 | Taniike et al. |
| 6,977,722 B2 | 12/2005 | Wohlstadter et al. |
| D515,220 S | 2/2006 | Miller et al. |
| 7,004,184 B2 | 2/2006 | Handique et al. |
| 7,008,796 B2 | 3/2006 | Wohlstadter et al. |
| 7,011,794 B2 | 3/2006 | Kagan et al. |
| 7,018,353 B2 | 3/2006 | Hunley et al. |
| 7,036,917 B2 | 5/2006 | Müller-Chorus et al. |
| 7,041,206 B2 | 5/2006 | Gephart et al. |
| 7,061,595 B2 | 6/2006 | Cabuz et al. |
| 7,111,503 B2 | 9/2006 | Brumboiu et al. |
| 7,115,421 B2 | 10/2006 | Grzeda et al. |
| 7,135,547 B2 | 11/2006 | Gengrinovitch |
| 7,205,116 B2 | 4/2007 | Salamone et al. |
| 7,235,213 B2 | 6/2007 | Mpock et al. |
| 7,238,246 B2 | 7/2007 | Peters et al. |
| 7,247,488 B2 | 7/2007 | Ghai et al. |
| 7,277,166 B2 | 10/2007 | Padmanabhan et al. |
| 7,282,179 B2 | 10/2007 | Iwaki et al. |
| 7,285,425 B2 | 10/2007 | Shareef et al. |
| 7,288,195 B2 | 10/2007 | Coville et al. |
| 7,299,081 B2 | 11/2007 | Mace et al. |
| 7,306,727 B2 | 12/2007 | Perreault |
| 7,314,711 B2 | 1/2008 | Richter et al. |
| 7,329,538 B2 | 2/2008 | Waieright et al. |
| 7,335,339 B2 | 2/2008 | Brendtsson |
| 7,378,270 B2 | 5/2008 | Azarnia et al. |
| 7,384,409 B2 | 6/2008 | Fischer et al. |
| 7,399,637 B2 | 7/2008 | Wright et al. |
| 7,419,821 B2 | 9/2008 | Davis et al. |
| 7,422,903 B2 | 9/2008 | Conlon et al. |
| 7,422,905 B2 | 9/2008 | Clague et al. |
| 7,438,853 B2 | 10/2008 | Zen et al. |
| 7,439,017 B2 | 10/2008 | Heroux et al. |
| 7,439,069 B2 | 10/2008 | Nippoldt et al. |
| 7,471,394 B2 | 12/2008 | Padmanabhan et al. |
| 7,481,787 B2 | 1/2009 | Gable et al. |
| 7,485,153 B2 | 2/2009 | Padmanabhan et al. |
| 7,494,819 B2 | 2/2009 | Bahatt et al. |
| 7,497,997 B2 | 3/2009 | Glezer et al. |
| 7,521,247 B2 | 4/2009 | De Haan |
| 7,523,649 B2 | 4/2009 | Corey et al. |
| 7,547,384 B2 | 6/2009 | Keenan |

(56) References Cited

U.S. PATENT DOCUMENTS

| | | |
|---|---|---|
| 7,553,448 B2 | 6/2009 | Kumar et al. |
| 7,553,453 B2 | 6/2009 | Gu et al. |
| 7,569,346 B2 | 8/2009 | Petersen et al. |
| 7,569,393 B2 | 8/2009 | Sin |
| 7,595,169 B2 | 9/2009 | Swaim et al. |
| 7,604,777 B2 | 10/2009 | Columbus |
| 7,608,042 B2 | 10/2009 | Goldberger et al. |
| 7,630,063 B2 | 12/2009 | Padmanabhan et al. |
| 7,641,856 B2 | 1/2010 | Padmanabhan et al. |
| 7,666,355 B2 | 2/2010 | Alavie et al. |
| 7,682,511 B2 | 3/2010 | de los Reyes et al. |
| 7,682,788 B2 | 3/2010 | Sigal et al. |
| 7,723,099 B2 | 5/2010 | Miller et al. |
| 7,736,901 B2 | 6/2010 | Opalsky et al. |
| 7,767,794 B2 | 8/2010 | Salamone et al. |
| 7,771,658 B2 | 8/2010 | Larsen |
| 7,776,583 B2 | 8/2010 | Billadeau et al. |
| 7,781,226 B2 | 8/2010 | McDevitt et al. |
| 7,816,124 B2 | 10/2010 | Samsoondar |
| 7,820,102 B2 | 10/2010 | Myrick et al. |
| 7,822,510 B2 | 10/2010 | Paik et al. |
| RE41,946 E | 11/2010 | Anderson et al. |
| 7,824,925 B2 | 11/2010 | Wohlstadter et al. |
| 7,833,746 B2 | 11/2010 | Brendtsson et al. |
| 7,838,631 B2 | 11/2010 | Yamashita et al. |
| 7,859,670 B2 | 12/2010 | Kim et al. |
| 7,887,750 B2 | 2/2011 | Blatt et al. |
| 7,888,125 B2 | 2/2011 | Gibbons et al. |
| 7,901,629 B2 | 3/2011 | Calatzis et al. |
| 7,911,617 B2 | 3/2011 | Padmanabhan et al. |
| 7,914,994 B2 | 3/2011 | Petersen et al. |
| 7,923,256 B2 | 4/2011 | Widrig Opalsky et al. |
| 7,928,718 B2 | 4/2011 | Larsen |
| 7,932,098 B2 | 4/2011 | Childers et al. |
| 7,939,021 B2 | 5/2011 | Smith et al. |
| 7,952,069 B2 | 5/2011 | Shiokawa et al. |
| 7,977,106 B2 | 7/2011 | Widrig Opalsky et al. |
| 7,978,329 B2 | 7/2011 | Padmanabhan et al. |
| 7,981,362 B2 | 7/2011 | Glezer et al. |
| 7,985,589 B2 | 7/2011 | Garner et al. |
| 8,003,060 B2 | 8/2011 | Cracauer et al. |
| 8,007,670 B2 | 8/2011 | Connors, Jr. |
| 8,008,034 B2 | 8/2011 | Gibbons et al. |
| 8,012,744 B2 | 9/2011 | Gibbons et al. |
| 8,012,745 B2 | 9/2011 | Glezer et al. |
| 8,017,382 B2 | 9/2011 | Davis et al. |
| 8,021,873 B2 | 9/2011 | Johnson et al. |
| 8,028,566 B2 | 10/2011 | Larsen |
| 8,034,296 B2 | 10/2011 | Cox et al. |
| 8,046,175 B2 | 10/2011 | Kuo et al. |
| 8,071,051 B2 | 12/2011 | Padmanabhan et al. |
| 8,101,404 B2 | 1/2012 | Samsoondar |
| 8,101,431 B2 | 1/2012 | McDevitt et al. |
| 8,105,783 B2 | 1/2012 | Handique |
| 8,105,849 B2 | 1/2012 | McDevitt et al. |
| 8,137,626 B2 | 3/2012 | Maltezos et al. |
| 8,236,555 B2 | 8/2012 | Stromgren et al. |
| 8,273,566 B2 | 9/2012 | Billadeau et al. |
| 8,343,526 B2 | 1/2013 | Billadeau et al. |
| 8,394,595 B2 | 3/2013 | Jung et al. |
| 8,394,608 B2 | 3/2013 | Ririe et al. |
| 8,481,901 B2 | 7/2013 | Bedingham et al. |
| 8,585,279 B2 | 11/2013 | Rida |
| 8,623,638 B2 | 1/2014 | Solomon |
| 8,747,779 B2 | 6/2014 | Sprague et al. |
| 8,772,017 B2 | 7/2014 | Battrell et al. |
| 8,778,665 B2 | 7/2014 | Gibbons et al. |
| 8,846,310 B2 | 9/2014 | Johnson et al. |
| 8,870,446 B2 | 10/2014 | Rida |
| 8,895,295 B2 | 11/2014 | Ririe et al. |
| 8,940,230 B2 | 1/2015 | Kuhnl et al. |
| 2002/0019060 A1 | 2/2002 | Petersen et al. |
| 2002/0045243 A1 | 4/2002 | Laska et al. |
| 2002/0098116 A1 | 7/2002 | Sugaya et al. |
| 2002/0143297 A1 | 10/2002 | Francavilla et al. |
| 2002/0155033 A1 | 10/2002 | Strand et al. |
| 2003/0029254 A1 | 2/2003 | Hvidtfeldt et al. |
| 2003/0035758 A1 | 2/2003 | Buechler et al. |
| 2003/0052054 A1 | 3/2003 | Pearl et al. |
| 2003/0073089 A1 | 4/2003 | Mauze et al. |
| 2003/0185707 A1 | 10/2003 | Iwaki et al. |
| 2003/0224523 A1 | 12/2003 | Thornberg et al. |
| 2004/0035792 A1 | 2/2004 | Rauch et al. |
| 2004/0086872 A1 | 5/2004 | Childers et al. |
| 2004/0096368 A1 | 5/2004 | Davis et al. |
| 2004/0176704 A1 | 9/2004 | Stevens et al. |
| 2004/0228765 A1 | 11/2004 | Witty et al. |
| 2004/0228766 A1 | 11/2004 | Witty et al. |
| 2004/0248284 A1 | 12/2004 | Van Beuningen |
| 2004/0259268 A1 | 12/2004 | Jacobs et al. |
| 2005/0014279 A1 | 1/2005 | Nguyen et al. |
| 2005/0042137 A1 | 2/2005 | Petersen et al. |
| 2005/0074900 A1 | 4/2005 | Morgan et al. |
| 2005/0181443 A1 | 8/2005 | Sun et al. |
| 2005/0220668 A1 | 10/2005 | Coville |
| 2005/0227370 A1 | 10/2005 | Ramel et al. |
| 2005/0245844 A1 | 11/2005 | Mace et al. |
| 2005/0250173 A1 | 11/2005 | Davis et al. |
| 2006/0094028 A1 | 5/2006 | Danna et al. |
| 2006/0165558 A1 | 7/2006 | Witty et al. |
| 2006/0177347 A1 | 8/2006 | Larsen et al. |
| 2006/0218010 A1 | 9/2006 | Michon et al. |
| 2006/0228259 A1 | 10/2006 | Samsoondar |
| 2006/0257854 A1 | 11/2006 | McDevitt et al. |
| 2006/0257941 A1 | 11/2006 | McDevitt et al. |
| 2006/0257991 A1 | 11/2006 | McDevitt et al. |
| 2006/0263818 A1 | 11/2006 | Scherer et al. |
| 2006/0275841 A1 | 12/2006 | Blankfard et al. |
| 2007/0003434 A1 | 1/2007 | Padmanabhan et al. |
| 2007/0009386 A1 | 1/2007 | Padmanabhan et al. |
| 2007/0031283 A1 | 2/2007 | Davis et al. |
| 2007/0036026 A1 | 2/2007 | Laibinis et al. |
| 2007/0116600 A1 | 5/2007 | Kochar et al. |
| 2007/0166195 A1 | 7/2007 | Padmanabhan et al. |
| 2007/0166196 A1 | 7/2007 | Bardell et al. |
| 2007/0166725 A1 | 7/2007 | McBride et al. |
| 2007/0172388 A1 | 7/2007 | Padmanabhan et al. |
| 2007/0178514 A1 | 8/2007 | Van Beuningen |
| 2007/0178521 A1 | 8/2007 | Sakaino et al. |
| 2007/0248497 A1 | 10/2007 | Robillot |
| 2007/0292941 A1 | 12/2007 | Handique et al. |
| 2008/0021296 A1 | 1/2008 | Creaven |
| 2008/0025872 A1 | 1/2008 | Dykes et al. |
| 2008/0057572 A1 | 3/2008 | Petersen et al. |
| 2008/0131322 A1 | 6/2008 | Kheiri et al. |
| 2008/0149840 A1 | 6/2008 | Handique et al. |
| 2008/0153078 A1 | 6/2008 | Braman et al. |
| 2008/0188732 A1 | 8/2008 | Mace et al. |
| 2008/0227219 A1 | 9/2008 | Gamez |
| 2008/0311002 A1 | 12/2008 | Kirby et al. |
| 2009/0018411 A1 | 1/2009 | Mace et al. |
| 2009/0047713 A1 | 2/2009 | Handique |
| 2009/0065357 A1 | 3/2009 | Glezer et al. |
| 2009/0081078 A1 | 3/2009 | Caramuta |
| 2009/0098541 A1 | 4/2009 | Southern et al. |
| 2009/0130658 A1 | 5/2009 | Barlag et al. |
| 2009/0130719 A1 | 5/2009 | Handique |
| 2009/0148882 A1 | 6/2009 | Goldstein |
| 2009/0151792 A1 | 6/2009 | Noda |
| 2009/0181864 A1 | 7/2009 | Nguyen et al. |
| 2009/0215072 A1 | 8/2009 | McDevitt et al. |
| 2009/0221059 A1 | 9/2009 | Williams et al. |
| 2009/0246076 A1 | 10/2009 | Kumar et al. |
| 2009/0253130 A1 | 10/2009 | Yoo |
| 2009/0311736 A1 | 12/2009 | Ciotti et al. |
| 2009/0325276 A1 | 12/2009 | Battrell et al. |
| 2010/0029011 A1 | 2/2010 | Sin |
| 2010/0075311 A1 | 3/2010 | Barrault et al. |
| 2010/0081144 A1 | 4/2010 | Holmes et al. |
| 2010/0112723 A1 | 5/2010 | Battrell et al. |
| 2010/0117666 A1 | 5/2010 | Wada et al. |
| 2010/0158756 A1 | 6/2010 | Taylor et al. |
| 2010/0159556 A1 | 6/2010 | Rida |
| 2010/0173394 A1 | 7/2010 | Colston, Jr. et al. |

(56) References Cited

U.S. PATENT DOCUMENTS

| | | |
|---|---|---|
| 2010/0180980 A1 | 7/2010 | Lee et al. |
| 2010/0197522 A1 | 8/2010 | Liu et al. |
| 2010/0203521 A1 | 8/2010 | Klapperich et al. |
| 2010/0203550 A1 | 8/2010 | Miller et al. |
| 2010/0227412 A1 | 9/2010 | Cerda |
| 2010/0240022 A1 | 9/2010 | McNeely |
| 2010/0261292 A1 | 10/2010 | Glezer et al. |
| 2010/0262304 A1 | 10/2010 | Gonnella et al. |
| 2010/0282609 A1 | 11/2010 | Pollack et al. |
| 2010/0285578 A1 | 11/2010 | Selden et al. |
| 2010/0290952 A1 | 11/2010 | Koike et al. |
| 2010/0291588 A1 | 11/2010 | McDevitt et al. |
| 2010/0303722 A1 | 12/2010 | Jin et al. |
| 2011/0008908 A1 | 1/2011 | Biesbrouck |
| 2011/0016691 A1 | 1/2011 | Alden et al. |
| 2011/0039298 A1 | 2/2011 | Berndtsson et al. |
| 2011/0067489 A1 | 3/2011 | Haberstroh et al. |
| 2011/0091357 A1 | 4/2011 | Blatt et al. |
| 2011/0100101 A1 | 5/2011 | Zenhausern et al. |
| 2011/0143378 A1 | 6/2011 | Putnam |
| 2011/0171754 A1 | 7/2011 | Redmond et al. |
| 2011/0192218 A1 | 8/2011 | Miyamura et al. |
| 2011/0192219 A1 | 8/2011 | Miyamura et al. |
| 2011/0194977 A1 | 8/2011 | Miyamura et al. |
| 2011/0195490 A1 | 8/2011 | Kang et al. |
| 2011/0195495 A1 | 8/2011 | Selden et al. |
| 2011/0201099 A1 | 8/2011 | Anderson et al. |
| 2011/0201909 A1 | 8/2011 | Emery et al. |
| 2011/0203924 A1 | 8/2011 | Wohlstadter et al. |
| 2011/0259091 A1 | 10/2011 | Laubscher et al. |
| 2011/0269159 A1 | 11/2011 | Campbell et al. |
| 2011/0269222 A1 | 11/2011 | Miller et al. |
| 2011/0290669 A1 | 12/2011 | Davis et al. |
| 2011/0294224 A1 | 12/2011 | Liu |
| 2011/0312553 A1 | 12/2011 | Silverbrook et al. |
| 2011/0312661 A1 | 12/2011 | Silverbrook et al. |
| 2011/0312742 A1 | 12/2011 | Silverbrook et al. |
| 2011/0318774 A1 | 12/2011 | Larsen |
| 2012/0003730 A1 | 1/2012 | Padmanabhan et al. |
| 2012/0009667 A1 | 1/2012 | Peterson et al. |
| 2012/0034624 A1 | 2/2012 | Miller et al. |
| 2012/0034645 A1 | 2/2012 | Billadeau et al. |
| 2012/0043202 A1 | 2/2012 | Miyamura et al. |
| 2012/0045375 A1 | 2/2012 | Miyamura et al. |
| 2012/0051972 A1 | 3/2012 | Joseph |
| 2012/0053335 A1 | 3/2012 | Liu et al. |
| 2012/0115213 A1 | 5/2012 | Hofstadler et al. |
| 2012/0141337 A1 | 6/2012 | Maltezos et al. |
| 2012/0177537 A1 | 7/2012 | Aota et al. |
| 2012/0190128 A1 | 7/2012 | Nikbakht et al. |
| 2012/0190589 A1 | 7/2012 | Anderson et al. |
| 2012/0252138 A1 | 10/2012 | Sasso, Jr. et al. |
| 2013/0137172 A1 | 5/2013 | Ririe et al. |
| 2014/0017709 A1 | 1/2014 | Lowe et al. |
| 2014/0186935 A1 | 7/2014 | Yoo |
| 2014/0329301 A1 | 11/2014 | Handique |

FOREIGN PATENT DOCUMENTS

| | | |
|---|---|---|
| EP | 1489303 B1 | 12/2004 |
| EP | 2007905 B1 | 12/2008 |
| EP | 2281631 B1 | 2/2011 |
| EP | 2419217 B1 | 2/2012 |
| GB | 2112293 | 7/1983 |
| JP | 2010-237050 | 10/2010 |
| WO | 8706706 | 11/1987 |
| WO | 9005302 | 5/1990 |
| WO | 9419683 | 9/1994 |
| WO | 9419684 | 9/1994 |
| WO | 9508644 | 3/1995 |
| WO | 9621154 | 7/1996 |
| WO | 9635697 | 11/1996 |
| WO | 9635812 | 11/1996 |
| WO | 9641177 | 12/1996 |
| WO | 9915694 | 4/1999 |
| WO | 00/72970 | 12/2000 |
| WO | 2005095954 A1 | 10/2005 |
| WO | 2006069328 A2 | 6/2006 |
| WO | 2007002579 A2 | 1/2007 |
| WO | 2007005626 | 1/2007 |
| WO | 2011008972 A1 | 1/2011 |
| WO | 2011027092 A1 | 3/2011 |
| WO | 2011113569 | 9/2011 |
| WO | 2012024543 A1 | 2/2012 |
| WO | 2012058632 A1 | 5/2012 |
| WO | 2012136695 A1 | 10/2012 |
| WO | 2013082273 A1 | 6/2013 |
| WO | 2013136115 A1 | 9/2013 |
| WO | 2013173524 A2 | 11/2013 |
| WO | 2013173525 A1 | 11/2013 |
| WO | 2014043388 A1 | 3/2014 |

OTHER PUBLICATIONS

Bertino, et al., "5-Fluorouracil Drug Management: Pharmacokinetics and Pharmacogenomics Workshop Meeting Summary; Orlando, Florida; Jan. 2007", Clinical Colorectal Cancer, vol. 6(6):407-422 (2007).

Bertucci, et al., "The Binding of 5-fluorouracil to Native and Modified Human Serum Albumin: UV, CD, and 1H and 19F NMR Investigation", Journal of Pharmaceutical and Biomedical Analysis, vol. 13:1087-1093 (1995).

Beumer, et al., "A Rapid Nanoparticle Immunoassay to Quantitate 5-Fluorouracil (5-FU) in Plasma", ASCO GI 2008 Meeting (Poster).

Crowley, et al., "Isolation of Plasma from Whole Blood Using Planar Microfilters for Lab-on-a-Chip Applications", Lab Chip, vol. 5(9):922-929 (2005).

Jaffrin, M.Y. (1995). Biological Flows. M.Y. Jaffrin and Colin Caro (Eds.). Plenum Press, New York, pp. 199-226.

Joseph, et al., "Evaluation of Alternatives to Warfarin as Probes for Sudlow Site I of Human Serum Albumin Characterization by High-Performance Affinity Chromatography", J. Chromatogr. A., vol. 1216(16):3492-3500 (2009).

Lukas, et al. , "Binding of Digitoxin and Some Related Cardenolides to Human Plasma Proteins", The Journal of Clinical Investigation, vol. 48:1041-1053 (1969).

Madsen, et al., "Cooperative Interaction of Warfarin and Phenylbutazone with Human Serum Albumin", Biochemical Pharmacology, vol. 30(11):1169-1173 (1981).

Means, et al. (1982). Modification of Proteins: Food, Nutritional, and Pharmacological Aspects. Robert E. Feeny and John R. Whitaker (Eds.). American Chemical Society. pp. 325-346.

Olympus UK Ltd—Diagnostics Laboratory News Directory, http://www.labnewsdirectory.co.uk/company/Olympus-UK-Ltd-Diagnostics/2232, (Oct. 1, 2009).

Peters, T., Jr., "Serum Albumin", Adv. Protein Chem., vol. 37:161-246 (1985).

Peyrin, et al., "Characterization of Solute Binding at Human Serum Albumin Site II and its Geometry Using a Biochromatographic Approach", Biophysical Journal, vol. 77:1206-1212 (1999).

Saif, et al. "Pharmacokinetically Guided Doe Adjustment of 5-Fluorouracil: A Rational Approach to Improving Therapeutic Outcomes", J. Natl. Cancer Inst., vol. 101:1543-1552 (2009).

Salamone, et al., "Novel Monoclonal Antibodies for Measuring 5-Fluorouracil Concentrations in Biological Fluids", Journal of Clinical Oncology, 2006 ASCO Annual Meeting Proceedings (Post-Meeting Edition); vol. 24(18S):2055 (2006).

Salamone, et al., "A Multi-Center Evaluation of a Rapid Immunoassay to Quantitate 5-Fluorouracil in Plasma", 2008 HOPA Conference—Anaheim, California (Poster).

Sulkowska, et al., "Competitive Binding of Phenylbutazone and Colchicine to Serum Albumin in Multidrug Therapy: A Spectroscopic Study", Journal of Molecular Structure, vol. 881:97-106 (2008).

Vandelinder, V. and A. Groisman, "Separation of Plasma from Whole Human Blood in a Continuous Cross-Flow in a Molded Microfluidic Device", Anal. Chem., vol. 78:3765-3771 (2006).

(56) References Cited

OTHER PUBLICATIONS

Villamor, J. and A. Zatón, "Data Plotting of Warfarin Binding to Human Serum Albumin", J. Biochem. Biophys. Methods, vol. 48:33-41 (2001).
Vos, et al., "Use of the Enzyme-Linked Immunosorbent Assay (ELISA) in Immunotoxicity Testing", Environmental Health Perspectives, vol. 43:115-121 (1982).
Yamashita, et al., "5-Fluorouracil Derivatives with Serum Protein Binding Potencies", Chem. Pharm. Bull., vol. 37 (10):2861-2863 (1989).
Yamashita, et al., "Possible Role of Serum Protein Binding to Improve Drug Disposition", International Journal of Pharmaceutics, vol. 108:241-247 (1994).
Zsila, et al., "Evaluation of Drug-Human Serum Albumin Binding Interactions with Support Vector Machine Aided Online Automated Docking", Bioinformatics, vol. 27(13):1806-1813 (2011).
The International Search Report and the Written Opinion from International PCT Application No. PCT/US2013/041252.
The International Search Report and the Written Opinion from International PCT Application No. PCT/US2013/041255.
The International Search Report and the Written Opinion from International PCT Application No. PCT/US2012/067041.
Restriction Requirement, dated Jun. 27, 2014, from co-pending U.S. Appl. No. 13/844,450.
Response to Jun. 27, 2014 Restriction Requirement, from co-pending U.S. Appl. No. 13/844,450.
Restriction Requirement, dated Jul. 2, 2014, from co-pending U.S. Appl. No. 13/844,527.
Response to Jul. 2, 2014 Restriction Requirement, from co-pending U.S. Appl. No. 13/844,527.
Notice of Allowance and Fees Due, dated Oct. 22, 2014, from co-pending U.S. Appl. No. 13/844,450.
Notice of Allowance and Fees Due, dated Oct. 30, 2014, from co-pending U.S. Appl. No. 13/844,527.
Notice of Allowance and Fees Due, dated Jan. 5, 2015, from co-pending U.S. Appl. No. 13/844,450.
Notice of Allowance and Fees Due, dated Jan. 9, 2015, from co-pending U.S. Appl. No. 13/844,527.
Notice of Allowance and Fees Due, dated Mar. 3, 2015, from co-pending U.S. Appl. No. 13/844,450.
Notice of Allowance and Fees Due, dated Mar. 3, 2015, from co-pending U.S. Appl. No. 13/844,527.
The Australian Examination Report, dated Jun. 19, 2015, from AU Application No. 2013262816 (a co-pending application to U.S. Appl. No. 14/401,278).
Notice of Allowance, dated Aug. 20, 2015, from co-pending U.S. Appl. No. 14/401,275.
The European Extended Search Report, dated Dec. 23, 2015, from EP Application No. 13790774.7 (a copending application to U.S. Appl. No. 14/401,278).
As-filed Response to Australian Examination Report of Sep. 10, 2015, from AU Application No. 2013262815 (a co-pending application to U.S. Appl. No. 14/401,278).
Australian Examination Report, dated Sep. 10, 2015, from AU Application No. 2013262815 (a co-pending application to U.S. Appl. No. 14/401,278).
European Extended Search Report, dated Dec. 23 2015, from EP Application No. 13790062.7 (a co-pending application to U.S. Appl. No. 14/401,278).
As-filed Response to the European Extended Search Report, dated Dec. 23 2015, from EP Application No. 13790062.7 (a co-pending application to U.S. Appl. No. 14/401,278).
As-filed Response to the European Extended Search Report, dated Dec. 23 2015, from EP Application No. 13790774.7 (a co-pending application to U.S. Appl. No. 14/401,278).
Notice of Acceptance, dated Jun. 14, 2016, from AU Application No. 2013262816 (a co-pending application to U.S. Appl. No. 14/401,278).
Certificate of Grant, dated Oct. 6, 2016, from AU Application No. 20132622816 (a co-pending application to U.S. Appl. No. 14/401,278).

CLINICAL DIAGNOSTIC SYSTEMS

CROSS-REFERENCE TO RELATED APPLICATIONS

This is a national stage application of International Application No. PCT/US2013/041255, filed internationally on May 15, 2013, which claims priority to U.S. Provisional Patent Application No. 61/647,272, filed May 15, 2012, which is herein incorporated by reference in its entirety. International PCT Application No. PCT/US2013/041255 is a continuation-in-part of each of International PCT Application No. PCT/US2012/067041, filed Nov. 29, 2012; U.S. patent application Ser. Nos. 13/844,450 and 13/844,527, both filed Mar. 15, 2013; and International PCT Application No. PCT/US2013/041252, filed May 15, 2013; each of which is herein incorporated by reference in its entirety.

BACKGROUND

In the healthcare industry, diagnostic testing is essential for properly diagnosing medical issues. Accuracy and precision are necessary to provide proper diagnoses. In order to provide accuracy and precision, diagnostic systems have been created to analyze samples in laboratories, clinics, hospitals, physicians' offices, etc.

Providing clinical point-of-care diagnostic systems, as well as other diagnostic systems also requires ease of use and fail safe mechanisms in order to decrease the frequency and intensity of user errors, which may lead to inaccurate diagnoses.

Furthermore, the size and scale of the diagnostic systems is also important. In order to be able to use diagnostic systems in certain settings, compactness may also be needed. To this end, the system may include both an instrument and separate cartridges used to provide samples to the instrument in the diagnostic systems. The cartridges may also need to be designed to assist in the compactness of the instrument.

Additionally, design of the cartridges used to provide samples to the diagnostic systems may also be designed to require less biological sample for testing, as well as be designed with ease of use and with fail safe mechanisms to further assist in the accuracy of diagnoses.

SUMMARY

Diagnostic systems, which include an instrument and associated cartridges, are provided herein. The diagnostic systems can provide accuracy and precision, ease of use with fail safe mechanisms, and compactness of scale.

As disclosed herein, embodiments of diagnostic systems may include clinical diagnostic instruments that can be configured to accept samples via cartridges, process samples within the cartridges, conduct tests on the samples while the samples remain within the cartridges, and provide diagnostic results.

Also disclosed herein, embodiments of the diagnostic system may be self-contained diagnostic systems in that a closed fluidic loop between an instrument and a cartridge containing a sample may be used. By providing self-contained diagnostic systems, the instrument can be maintained by disposing of the contents of the cartridge back into the cartridge, which can leave the instrument ready for another cartridge and test.

Furthermore, as disclosed herein, embodiments of diagnostic systems may include electrochemiluminescence (ECL) detectors to accurately and precisely analyze samples provided via cartridges. ECL detectors may include detectors similar to ones used in U.S. Pat. Nos. 5,700,427, 5,296,191, and 5,624,637, which are each incorporated herein by reference.

In embodiments disclosed herein, an in vitro diagnostic system is provided that is designed for use in Point of Care (POC) settings. Example embodiments can provide rapid, real-time test results for a variety of clinically important analytes. Example embodiments can also perform immunoassays using ECL-based detection technology. In example embodiments, assays may be available in single-use, disposable cartridges, which may contain all the reagents required to perform a test. In example embodiments, there may be no sample processing before a test is performed can be provided. For example, blood collection holders, such as a standard blood tube may be inserted directly into an example cartridge without any processing, such as centrifuging, and the cartridge along with a blood collection holder may be placed into the instrument for processing. Results can be available within 15 minutes, depending on the number of tests being run with in the cartridge.

In embodiments disclosed herein, example diagnostic systems can provide central laboratory quality results in an easy to use, low cost system.

In example embodiments, a diagnostic system having an instrument including an ECL detector; and a cartridge configured to fit within a portion of the instrument is provided. In example embodiments, the cartridge can include at least one reagent including an ECL label; and a blood collection holder.

In example embodiments, a system having a diagnostic instrument including a pump; an ECL detector; an incubator; a magnet; and an output device is provided. Additionally, the system may also have a cartridge configured to fit within a portion of the diagnostic instrument; a sample holder configured to fit within the cartridge; and a closed fluidic loop between the diagnostic instrument and the cartridge when the cartridge is fit within a portion of the diagnostic instrument, wherein the cartridge is configured to accept a sample from the sample holder and place the sample in fluidic communication with the diagnostic instrument via the closed fluidic loop.

In example embodiments, a method of providing POC services, which can include the steps of providing a biological sample; introducing the biological sample to a cartridge; providing the cartridge to a diagnostic instrument comprising an ECL detector; mixing the biological sample with a reagent in the cartridge to form a biological sample-reagent mixture; analyzing the biological sample-reagent mixture using the ECL detector; and outputting the results from the analyzing step is provided.

BRIEF DESCRIPTION OF THE DRAWINGS

The accompanying drawings, which are incorporated and constitute a part of this specification, illustrate an embodiment of the invention. In the drawings.

DETAILED DESCRIPTION

Figure 1:
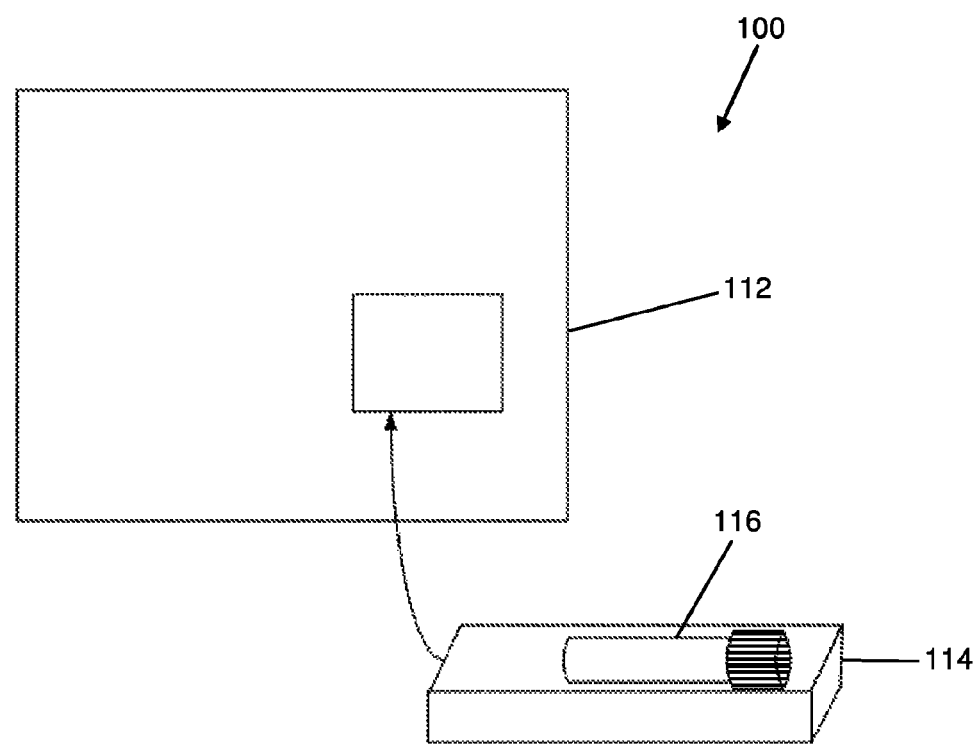
FIG. 1 is an overview illustration of an example diagnostic system.

The following detailed description refers to the accompanying drawings. The same reference numbers in different drawings may identify the same or similar elements. Also, the following detailed description describes embodiments of the invention and is not intended to limit the invention. Instead, the scope of the invention is defined by the appended claims and equivalents.

A. Overview

Provided herein is a clinical diagnostic system that includes a cartridge and an instrument. The clinical diagnostic system can provide accuracy and precision of test results, ease of system use, including fail safe mechanisms, and compactness in terms of scale. By providing a robust system that utilizes ECL technology with an efficient and accurate instrument and cartridge, users of the system can be assured accurate results with very little training or set up.

In embodiments disclosed herein, a clinical diagnostic system can provide rapid, real-time test results for a variety of clinically important analytes. Example clinical diagnostic system embodiments can perform immunoassays using ECL-based detection technology with assays available in disposable cartridges, which may contain all the reagents required to perform a test.

B. Definitions

The following are definitions of terms related to a diagnostic system in general.

The term "assay construction" as used herein is intended to include a step-by-step process of conducting an assay whether manual or automated. Assay construction may involve laboratory operations, such as pipetting, dispensing, metering, aliquoting, washing, free-bound separations, dialyzing, filtering, collecting, fractionating, diluting, mixing, incubating, processing, and the like.

The term "assay composition" as used herein is intended to include a complete set or subset of the necessary reagents or substances useful for an assay when combined. An assay composition may include an initial composition prior to assay construction, a composition immediately after initiating assay construction, a final mixture after assay construction, or a composition at any intermediate step of assay construction.

The term "bead(s)" as used herein is intended to include microscopic particles, such as superparamagnetic particles, magnetic microparticles, magnetic nanoparticles, or other particles of microscopic size. A bead may be spherical, though the shape is not limited and may include other shapes like spheroid, irregular particles, cubes, irregular cubes, and disks. The size range may cover from 1 nanometer to 10 microns in width.

The term "closed loop control" as used herein is intended to include a control module with one or more sensors to modulate a diagnostic system response. The term "open loop control" is contrasted with "closed loop control" and "open loop control" includes modules that do not provide a feedback signal to modulate a system response.

The term "dead volume" as used herein is intended to include a volume of a liquid trapped within a designated compartment, such as a sample holder or a reservoir, which may be unrecoverable.

The term "disposable" as used herein is intended to include items, such as single-use cartridges, which can be disposable after initial use and can contain an amount of reagents sufficient for testing a single biological sample before disposal of the cartridge.

The term "fluidic element" as used herein is intended to include a structure to hold, carry, or allow transport of a fluid. Fluidic elements may include pipes, channels, wells, reservoirs, conduits, valves, vents, flow paths, dispersers, pipettes, funnels, filters, and/or passageways.

The term "fluidic communication" as used herein is intended to include fluidic elements that may be in fluidic communication with other fluidic elements if the fluidic elements are connected via a channel, passageway, pathway, conduit, flow path or other fluidic element. Further, fluidic elements may also be in fluidic communication if they are connectable or transferable by a pipette or other transferable means, for example. Further, adjacent or nearby fluidic elements which liquid may be dispensed or transferred by pipette between or from one to the other may be in fluidic communication.

The term "fluorescence" as used herein is intended to include any emission of electromagnetic radiation, including ultraviolet or visible light, stimulated in a substance by the absorption of incident radiation and persisting only as long as the stimulating radiation is continued.

The term "fluorophore" as used herein refers to a substance that is fluorescent.

The term "fluorescent label" as used herein is intended to include a fluorophore used in the detection or measurement of fluorescence. A substance which is fluorescent yet detected by another detection method, such as ECL, is not a fluorescent label. A fluorescent label is operative when measuring fluorescence. Fluorescent beads are intended to include fluorescent labeled beads.

The term "Point of Care" as used herein is intended to include places or people that include laboratories, clinics, hospitals, physicians offices, etc., as well as, health care providers, clinicians, or others who may deliver healthcare products and services.

The term "precise" as used herein is intended to include situations when reproducibility and repeatability of a characteristic may occur. The term "highly precise" as used herein is intended to include situations when a characteristic variation is small over many observations of the characteristic.

The term "processed" as used herein is intended to include materials that may have been altered from their original or unused state (in relation to a diagnostic system), such as, for example, combined or mixed with other materials, reagents, samples or a combination thereof.

The term "standardized quantity" as used herein is intended to include a known amount of a substance, where the amount might be mass, concentration, volume, number, or other physical quantity. The known amount may have been determined or may be traceable to a reference method, golden standard, National Institute of Standards and Technology (NIST) traceable standard, or other method or standard. A known amount of a substance may also be determined by comparing an analytical result to a calibrator.

C. Diagnostic System

FIG. 1 is an overview illustration of an example diagnostic system 100. As illustrated in FIG. 1, diagnostic system 100 may include an instrument 112, a cartridge 114, and a sample holder 116 within the cartridge 114. Example instruments 112 can be configured to accept example cartridges 114. Example instruments 112 can include ECL detection technology to detect analytes in samples. Example cartridges 114 can be configured to accept sample holders. Further discussion of instruments 112 and cartridges 114 will follow below.

Figure 2:
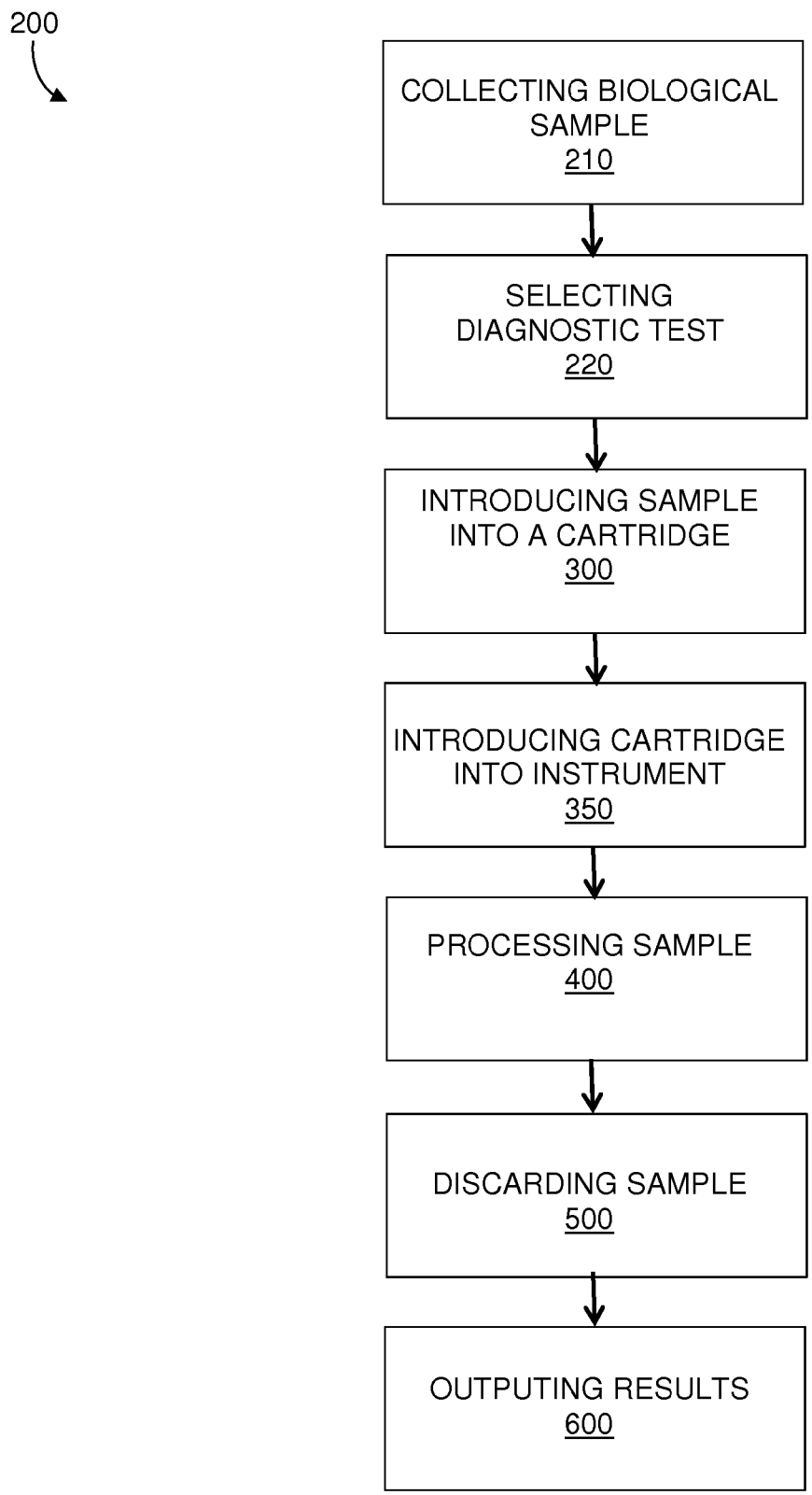
FIG. 2 is an overview illustration of an example method by which an example diagnostic system may be used.

FIG. 2 is an overview illustration of an example method 200 by which an example diagnostic system 100 may be used. As illustrated in FIG. 2, method 200 may include the step of collecting a biological sample 210. Example procedures for collecting a biological sample 210 may include any method available for gathering biological samples, such as venipuncture, finger stick, heel stick, arterial blood draw cannulation, etc. The biological samples may be gathered into a vial, tube, blood collection tube, and VACUTAINER® for example.

The step of collecting a biological sample 210 can also include verifying sample-patient identification. Verification can be confirmed by comparing sample identification with patient identification. For example, identification can be performed by comparing a label placed on a sample holder with a patient identification card or wrist band.

Method 200 may include the step of selecting a diagnostic test 220. Example procedures for selecting a diagnostic test 220 may include identifying information provided on a sample regarding a desired test or other processes of accessing selection of diagnostic tests information. For example, a sample vial may have a code or instructions indicating which tests should be run on the sample, and the selection of a diagnostic test can be directly identified and selected automatically or manually by an operator of instrument 112.

Method 200 may include the step of introducing a sample into a cartridge 300. Example procedures for introducing a sample into a cartridge 300 may include any method available for introducing a sample into a cartridge, such as inserting a blood collection tube into a preconfigured area of a cartridge. In embodiments discussed further below, the introducing a sample into a cartridge 300 may be provided as illustrated in FIG. 1, wherein sample holder 116 is configured to fit within a preconfigured section of cartridge 114. The preconfigured section, as an example, includes means for mounting sample holder such as a sample holder needle.

Figure 3:
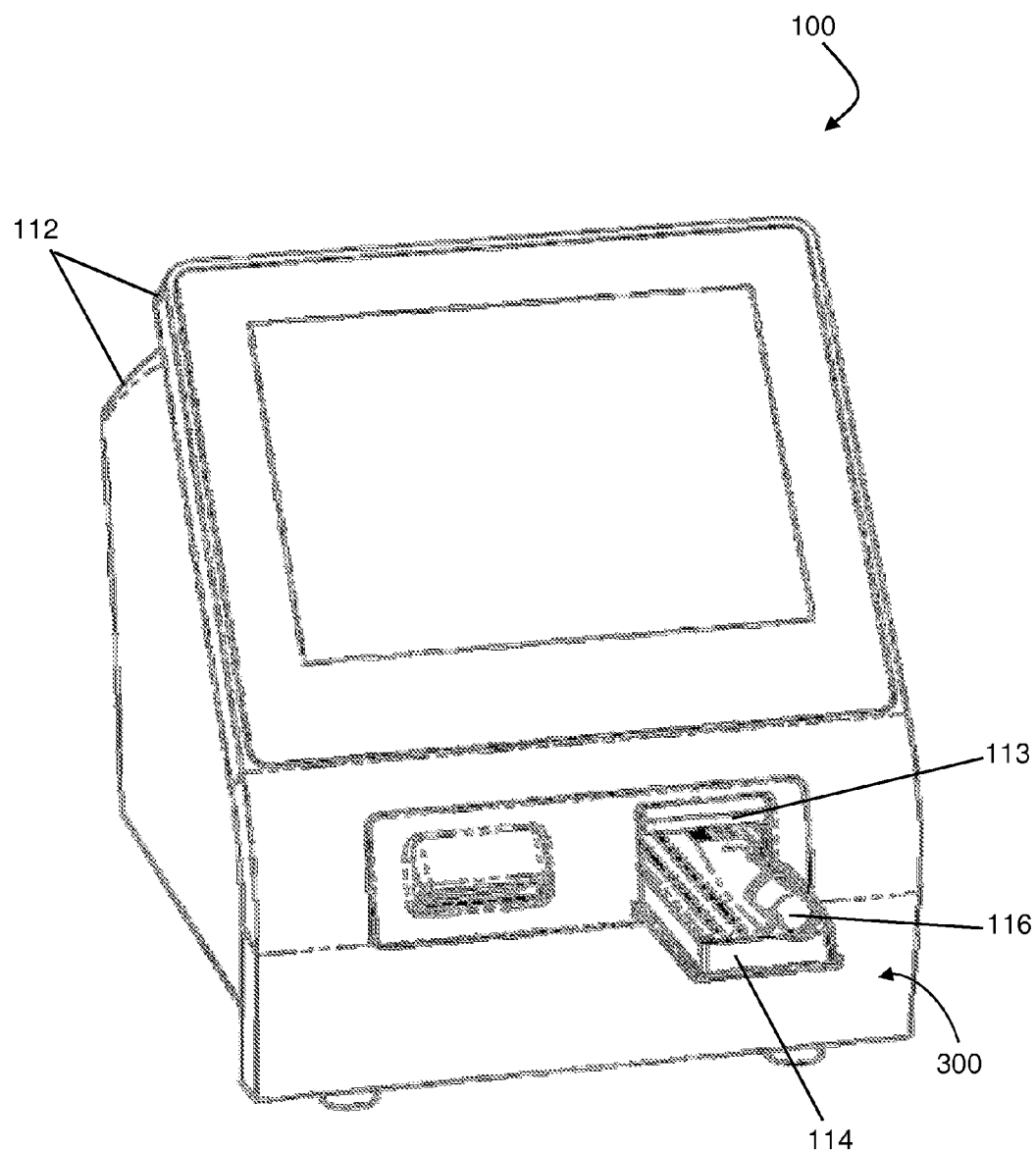
FIG. 3 is an illustration of an embodiment of a diagnostic system.

Method 200 may include the step of introducing a cartridge into an instrument 350. Example procedures for introducing a cartridge into an instrument 350 may include any method available for introducing a cartridge into an instrument, such as inserting a cartridge into a preconfigured area of an instrument. In embodiments discussed further below, the introducing a cartridge into an instrument 350 may be provided as illustrated in FIG. 1, wherein cartridge 114 is configured to fit within a preconfigured section of instrument 112. For example, as illustrated in FIG. 3, cartridge 114 may be inserted into slot 113 in instrument 112 of system 100.

Method 200 may include the step of processing a sample 400. Example procedures for processing a sample 400 may include any a series of sub-steps designed to construct an assay, analyze the sample, and provide information about the sample. In embodiments discussed further below, the processing a sample 400 may be provided as illustrated in FIG. 4.

Figure 4:
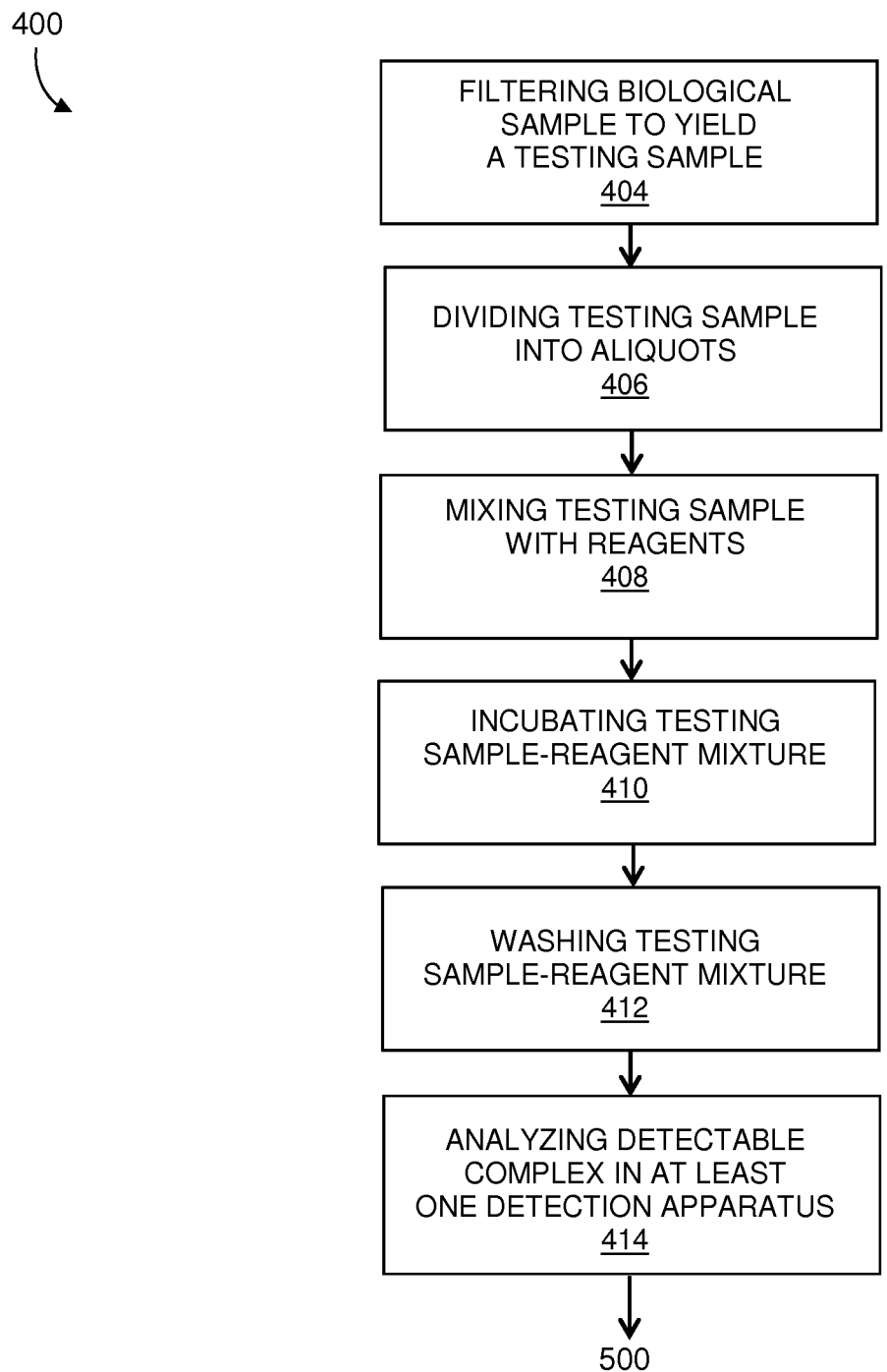
FIG. 4 is an overview illustration of an example method by which a biological sample is processed in a diagnostic system.

In FIG. 4, an embodiment of the step of processing a sample 400 can include several sub-steps 404 to 414, wherein each step is optional and can include additional sub-steps that may not be discussed herein.

The step of processing a sample 400 can include the sub-step of filtering a biological sample to yield a testing sample 404. Example procedures for filtering a biological sample 404 may include separating one part of a sample from another part. For example, filtering a whole blood biological sample may include separating plasma from whole blood.

Figure 5:
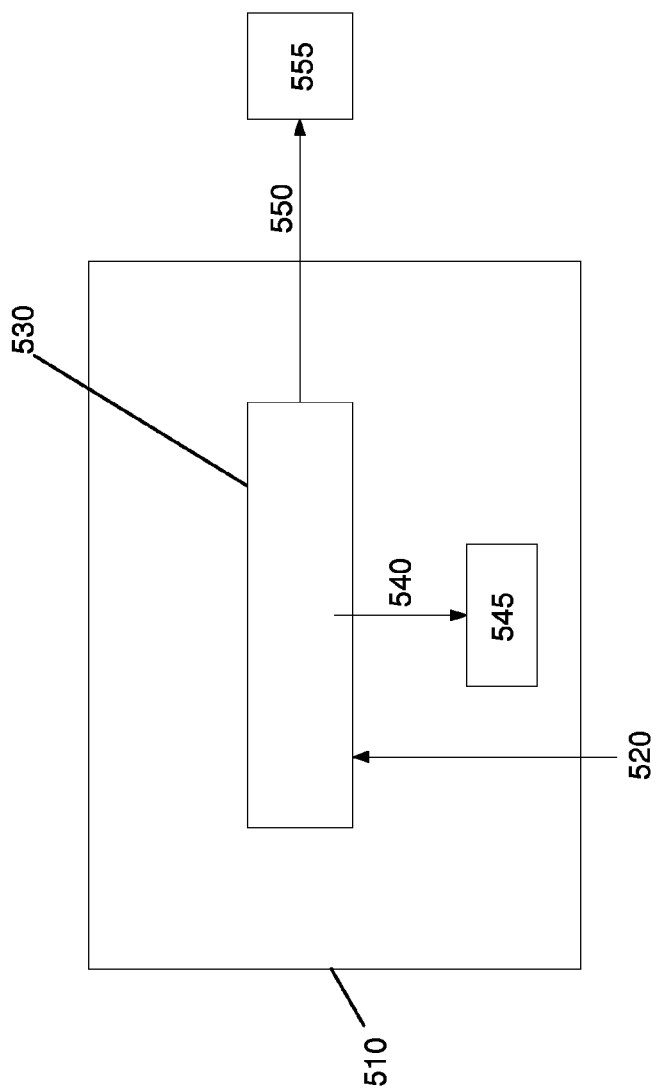
FIG. 5 is an illustration of an example filtration module

As illustrated in FIG. 5, a filtration module 510 can be provided to filter a biological sample. As illustrated in FIG. 5, a biological sample flow path 520 may be flowed through a filtration module 510. In example embodiments, the filtration module 510 can include one or more filters 530, where the biological sample flow path 520 is divided by the one or more filters 530 into a testing sample 540 and a waste product 550. The testing sample 540 can be collected into a testing sample cache 545. The waste product can be collected into a waste product collector 555. It is contemplated that the filtration module 510 can be configured to have one or more filtration layers within each filter 530, where the number and types of filtration layers 530 can depend on one or more targeted filtration factors, as well as structural integrity factors. For example, the number and types of filtration layers can depend on the targeted filtrate, the design and configuration of the cartridge, and/or the diagnostic system. Additionally, the filtration layers may include several layers of the same filtration material or different filtration materials.

Some embodiments of the diagnostic system 110 contemplate that a filtration module 510 can be situated within the cartridge 114. It is further contemplated that the filtration module 510 can be adapted to fit within cartridge 114. By providing the filtration module 510 within cartridge 114, a testing sample 540 (e.g., plasma) can be gathered without the need for centrifugation of the sample 400, for example. Further discussion of the filtration module 510 can be found in PCT/US2012/067041, which is hereby incorporated in its entirety by reference.

The step of processing a sample 400 can include the sub-step of dividing the testing sample 540 into aliquots 406. Once the testing sample 540 is in the desired form for use (e.g., filtered plasma), the testing sample 540 can be divided into volumes for further processing.

Aliquoting a testing sample 540 into multiple volumes may be desired when conducting a panel of assays or when conducting replicate measurements. Various embodiments of the diagnostic system 110 contemplate dividing the testing sample 540 into equal on non-equal volumes within the cartridge 114 for further processing.

Figure 6:
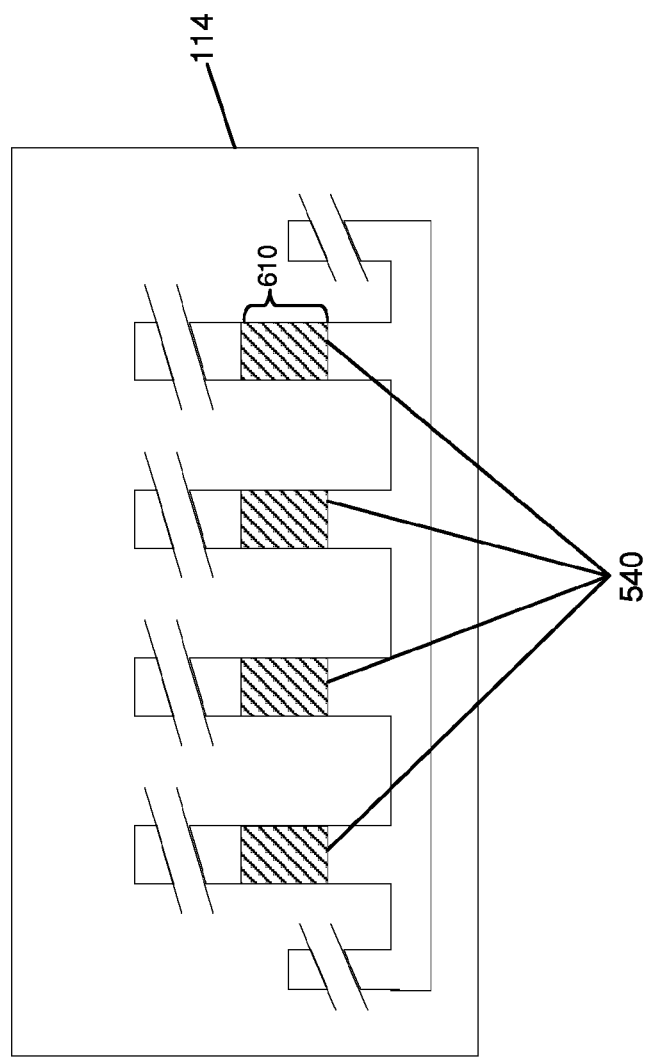
FIG. 6 in an illustration of an example of a testing sample that has been divided into volumes within the cartridge.

FIG. 6 illustrates an example of a testing sample 540 (shaded) that has been divided into equal volumes within the cartridge 114. An example method of dividing of the testing sample 540 can involve the use of a pump (not shown). For example, a pump may be provided as a component of the diagnostic instrument 112 to assist in controlling the movement of the testing sample 540 into the aliquoted volumes 610 within the cartridge 114. For example, the pump can create a vacuum within a portion of the cartridge 114 that can drive the testing sample 540 into the aliquoted volumes 610. In embodiments, it is contemplated that the particular pump can be chosen to control the accuracy and precision of the division of the testing sample 540 into aliquots.

It is further contemplated that a sensor (not shown), such as an optical sensor, can be used in conjunction with the pump to accurately position the testing sample 540 within the cartridge 114. The sensor can be a component of the diagnostic instrument 112 and may be positioned in such a way that it can detect the location of the testing sample 540 within the cartridge 114. For example, the sensor may be used to detect a transition between the presence of a fluid (e.g., the testing sample 540 or any other fluid) as compared to the presence of air or the lack of presence of the fluid. Additionally, it is further contemplated that feedback from the optical sensor can be translated into directions to tell the pump to stop or move the sample further.

The step of processing a sample 400 can include the sub-step of mixing the testing sample with reagents 408. Various embodiments of the diagnostic system 110 contemplate that a portion within the cartridge 114 can hold and store reagents 710 for a particular diagnostic test, as illustrated in FIG. 7.

Figure 7:
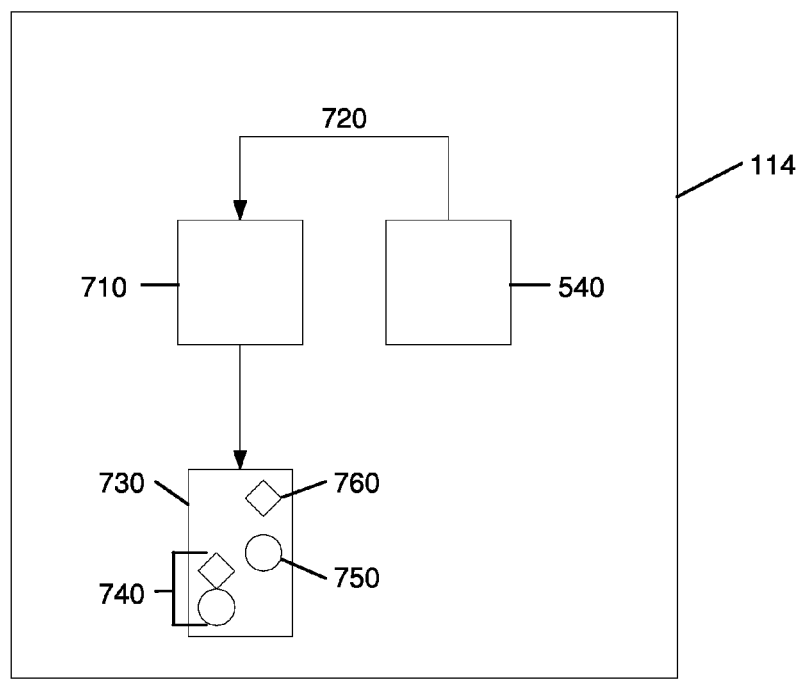
FIG. 7 is an illustration of components used in mixing the testing sample with reagents within a cartridge.

FIG. 7 is an illustration of components used in mixing the testing sample 540 with reagents 710 within a cartridge 114. The reagents 710 may be selected and measured into appropriate amounts depending on the intended purpose or goal of the diagnostic test. The pre-measured volumes of reagents 710 can be situated in various designated portions of a cartridge 114 for storage and use, such as in compartments, wells, and channels.

Reagents 710 may include an assay composition, beads, antibodies, binding partners, ligands, receptors, or detection label. Upon mixing reagents 710 with the testing sample 540, a testing sample-reagent mixture 730 can be formed.

Example assay compositions may include a biomarker that can attach to a targeted analyte. For example, 5-Fluorouracil (5-FU) is widely used in cancer patients to treat tumors including, but not limited to, colorectal, head and neck, stomach and breast carcinomas. 5-FU is most often administered systemically, but is also applied topically to treat some forms of pre-cancerous and cancerous skin disorders. In the case of 5-FU overdoses, a reagent with a biomarker specifically designed to attach to 5-FU may be provided. Further discussion of the biomarker for 5-FU may be found in PCT Application No. PCT/US12/67353, which is hereby incorporated in its entirety by reference.

With the assistance of a pump, the reagents 710 can be combined with the testing sample 540 within the cartridge 114. For example, aliquoted volumes 610 of the testing sample 540 can be moved along a mixing flow path 720 into a portion of the cartridge 114 holding the reagents 710, such as mixing well or a channel, as illustrated in FIG. 7. Within the portion of the cartridge 114 holding the reagents 710, an aliquoted volume 610 of the testing sample 540 can be supplied, so that the reagents 710 and the testing sample 540 within a testing sample-reagent mixture 730 can properly interact with each other in preparation for the diagnostic test analysis.

The testing sample-reagent mixture 730 can optionally include a reagent-reacted testing sample, or detectable complex 740, unreacted testing sample 750, and unreacted reagent 760. The detectable complex 740 can form in the mixing sub-step 408 and/or the incubating sub-step 410. The detectable complex 740 can have a labeled analyte attached, directly or indirectly, to a solid phase medium, such as a bead. The detectable complex 740 may include a detection label that can be read for analysis of the diagnostic test. For example, an ECL detection unit in a diagnostic system 110 may detect information about a detectable complex 740 by detecting a detection unit attached to an analyte. The unreacted testing sample 750 and the unreacted reagent 760 remain in the testing sample-reagent mixture 540 until removed or reacted.

In embodiments herein, the testing sample 540 and reagents 710 are preferably mixed thoroughly to create a homogeneous testing sample-reagent mixture 730 for diagnostic test accuracy. A homogeneous testing sample-reagent mixture 730 can refer to a testing sample-reagent mixture 730 that includes a maximum amount of analyte or antigen in the testing sample 540 being bound to the reagents 710, such that a maximum amount of detectable complex 740 is formed. A pump can be provided assist in agitating the combined testing sample-reagent mixture 730 within the cartridge 114 by creating movements (e.g., back and forth) to produce a homogeneous testing sample-reagent mixture 730.

The step of processing a sample 400 can include the sub-step of incubating the testing sample-reagent mixture 410. Various embodiments of a diagnostic system 110 contemplate incubating the testing sample-reagent mixture 730 once a homogeneous testing sample-reagent mixture 730 is achieved. The testing sample-reagent mixture 730 can be incubated by an incubator to allow formation of detectable complexes 740 from the unreacted sample 750 and the unreacted reagent 760 within the testing sample-reagent mixture 730. The testing sample-reagent mixture 730 can be incubated by an incubator apparatus that may be a component of the diagnostic instrument 112.

Figure 8:
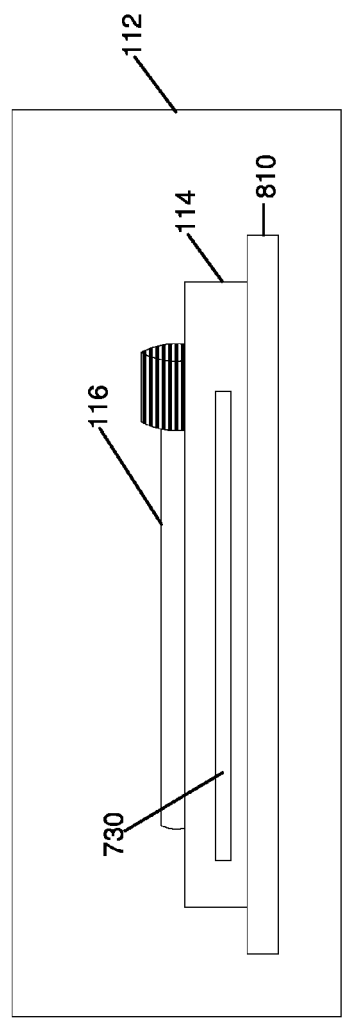
FIG. 8 is an illustration of an example cartridge positioned on an example incubator within an example instrument.

FIG. 8 is an illustration of an example cartridge 114 positioned on an example incubator 810 within an example instrument 112. As illustrated, the cartridge 114, which includes a homogeneous testing sample-reagent mixture 730, can be positioned near the incubator 810 within the instrument 112. For example, the cartridge 114 can be placed on the incubator 810 such that a lower region of the cartridge 114 may be adjacent to the incubator 810.

Incubation of a homogeneous testing sample-reagent mixture 730 can assist in providing optimal temperatures for the antigens and reagents to react and/or bind with one another. The incubator 810 can include one or more sensors to provide temperature measurements of the sample-reagent mixture 730 to ensure that a predetermined temperature is maintained. The incubator 810 can also include one or more heating and/or cooling elements to ensure that the temperature may be adjusted to maintain the predetermined temperature. For example, the incubator 810 can use a combination of heating elements, cooling elements, and sensors to provide an optimal temperature. In embodiments herein, the optimal temperature may be within a range (e.g., from about 25° C. to about 42° C.) or at a specific temperature (e.g., about 37° C.). It is contemplated that the predetermined temperature can be adjusted depending on the diagnostic test being run, as well as the reagents and sample being used. The time of the incubation can also be adjusted depending on the diagnostic test, reagents and sample being used.

Additionally, the incubator 810 can have multiple heating and/or cooling zones to heat and/or cool various portions of the cartridge 112. For example, separate heaters may be provided to heat a few zones simultaneously or consecutively. As another example, portions of the cartridge 112 can be moved to heating zones within the incubator 810 if the cartridge is moved within the instrument 112.

The step of processing a sample 400 can include the sub-step of washing the testing sample-reagent mixture 412. Various embodiments of the diagnostic system 110 contemplate washing the testing sample-reagent mixture 730 to isolate the detectable complex 740. For example, the washing sub-step 412 may remove any unreacted testing sample 760 and any unreacted reagents 760 from the testing sample-reagent mixture 730 to isolate a detectable complex 740.

By washing away the unreacted testing sample 750 and the unreacted reagent 760 from the testing sample-reagent mixture 730, the sensitivity and accuracy of the detection and analysis of the analyte or antigen (i.e., the detectable complex 740) within the diagnostic test can be increased. For example, the accuracy may be increased because the background noise can be substantially reduced by washing (e.g., the removal of the unreacted testing sample 750 and the unreacted reagent 760, both of which cause background noise). It is contemplated that substantially all of the unreacted testing sample 750 and the unreacted reagent 760 can be washed away. Examples herein provide that the unreacted testing sample 750 and the unreacted reagent 760 can be collected and contained within the cartridge 114 so that the washed sample can be introduced into a detection apparatus of the diagnostic instrument 112, thereby reducing the possibility of contamination between diagnostic tests.

In some embodiments, it is contemplated that the reagents 710 include a solid phase medium that can have a paramagnetic quality. By providing a solid phase medium that can have a paramagnetic quality, a magnet can be used in conjunction with the solid phase medium to magnetically fix a detectable complex 740 within a washing area while a rinsing fluid, such as a buffer, can be provided to remove the unwanted components and leave the detectable complex 740 behind.

Figure 9:
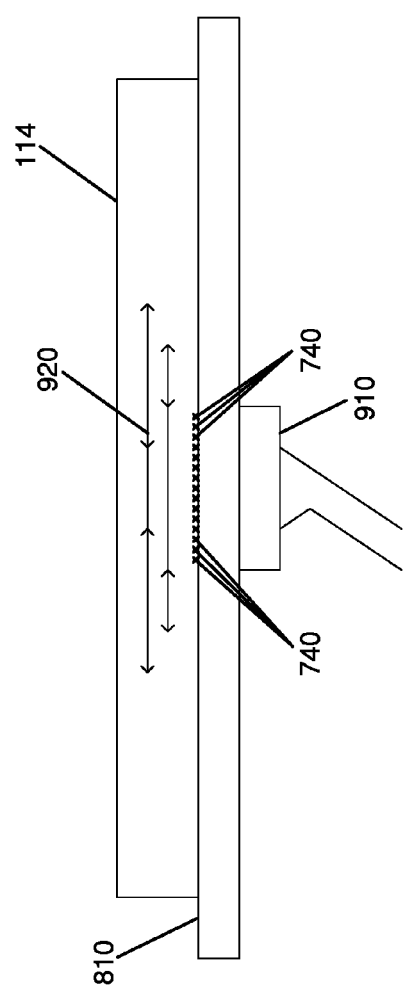
FIG. 9 is an illustration of an example cartridge provided with a magnet for use in an example washing step.

FIG. 9 is an illustration of an example cartridge 114 provided with a magnet 910 for use in an example washing sub-step 412. FIG. 9 includes a cartridge 114 with a magnet 910 holding a detectable complex 740 in place within a cartridge 114. Rinsing fluid 920 is also provided to wash away any unreacted testing sample 760 and any unreacted reagents 760 from the testing sample-reagent mixture 730 to expose a detectable complex 740.

The magnet 910 can be a component of the diagnostic instrument 112 and can be located within the diagnostic instrument 112 such that the magnet 910 and the cartridge 114 can come in close proximity.

A pump (not shown) of the diagnostic instrument 112 can assist in washing sub-step 412. The pump can move the testing sample-reagent mixture 730 within the cartridge 114 and can introduce additional fluids stored on the cartridge 114 to assist in rinsing. A sensor (not shown) may also assist in displacing and positioning fluids within the cartridge 114. It is also contemplated that during the washing of the testing sample-reagent mixture 730, incubation can also occur. For example, the incubator 810 may be located between or adjacent to the cartridge 114 and the magnet 910.

The step of processing a sample 400 can include the sub-step of analyzing a detectable complex in at least one detection apparatus 414. Analyzing the detectable complex can be done by using ECL technology to detect the detectable complex 740.

Figure 10A:
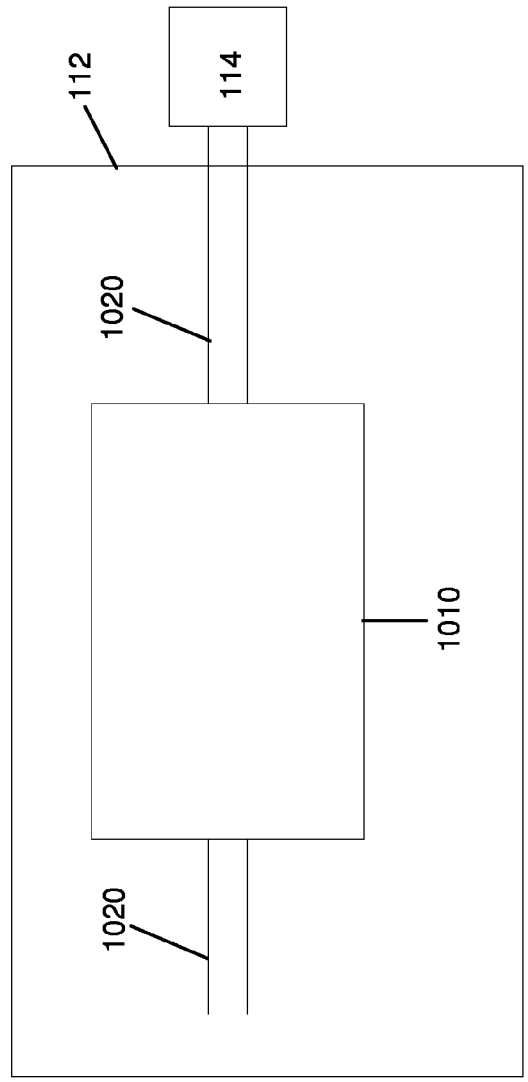
FIG. 10A is an illustration of a portion of an example instrument that can be used to analyze a sample.

FIG. 10A illustrates a detection apparatus 1010 within a diagnostic instrument 112. The detection apparatus 1010 can be connected to a cartridge 114 via a fluidic pathway 1020. In example embodiments, a detectable complex 740, as prepared in the cartridge 114 through sub-steps 404 through 412, can travel from the cartridge 114 via the pathway 1020 to the detection apparatus 1010.

It is contemplated that there may be more than one detection apparatus 1010 in a diagnostic instrument 112 or within a diagnostic system 110. In example diagnostic systems 110, detection apparatuses 1010 can be configured to meet different desired detection and analytical goals and to accommodate the diagnostic test being run. The type of detection and analysis can also vary depending on many factors, including, but not limited to, the diagnostic test being run and the desired specificity and sensitivity for the component being detected. The detection apparatus can use many different types of detection including ECL detection, chemiluminescence detection, fluorescence detection, time resolved fluorescence detection, fluorescence polarization detection, radiolabel detection, electrochemical detection, magnetic label detection, enzyme-linked immunosorbent assay detection, etc.

Figure 10B:
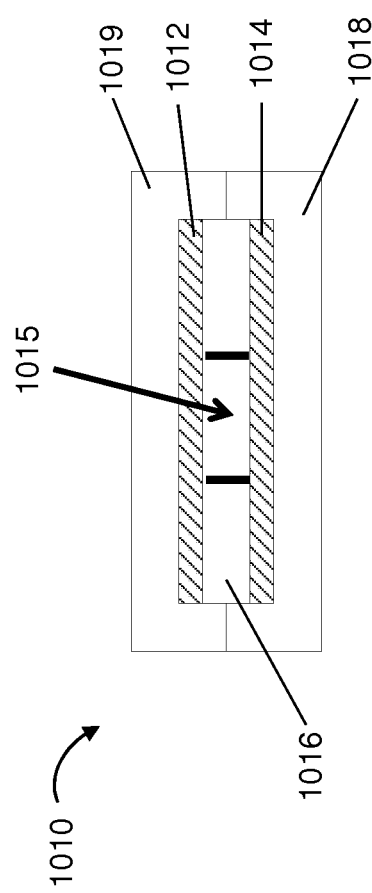
FIG. 10B is an illustration of a cross section of an example ECL detection apparatus in a diagnostic system.

ECL has been described in detail in the following U.S. Pat. Nos. 5,714,089, 6,165,729, 6,316,607, 6,312,896, 6,808,939, 6,881,589, 6,881,536, and 7,553,448, each of which is herein incorporated by reference in its entirety. FIG. 10B is an illustration of a cross section of an example ECL detection apparatus 1010 in a diagnostic system 110. The ECL-detection apparatus 1010 can include at least two electrodes 1012, 1014 separated by a gasket 1016 contained within a base 1018 that can be mated with a top 1020. A measurement containment area 1015, where the ECL detection can occur, can be formed in part by the arrangement of the gasket 1016 and the at least two electrodes 1012, 1014. The ECL detection apparatus 1010 can be a flow cell that also includes fluid ports to introduce a fluid for detection and a light source to assist in detecting a targeted analyte within the sample.

Typically, the ECL can operate as a flow cell so it is necessary for fluids to be introduced and extracted from the measurement containment area 1015 to set up the ECL reaction and flush out the ECL reagents. The measurement containment area 1015 can be a sealed volume with at least two fluid ports that can allow fluids to be pumped in and out of the sealed volume.

It is contemplated that the detectable complex 740 may include an ECL label bound to a magnetic bead, and the presence of the ECL label can be detected by ECL. It is contemplated that the number of ECL labels and/or the presence or absence of the ECL labels within the biological sample-reagent mixture can be detected using the ECL detector.

ECL signals may be generated by a redox reaction between an ECL label and a substrate. In certain embodiments, an ECL label can be a ruthenium-containing reagent. One example of a suitable ECL label is Tris(bypyridine) ruthenium(II) [Ru(bipy)3]2+, also referred to as TAG. In certain other embodiments, the substrate can be tripropylamine (TPA). Some advantages of the method of using ECL-based assays are they are rapid and sensitive. It is contemplated that for other detection methods, the detection label and reagents can be varied as necessary to satisfy the requirements of the detection method.

Figure 11:
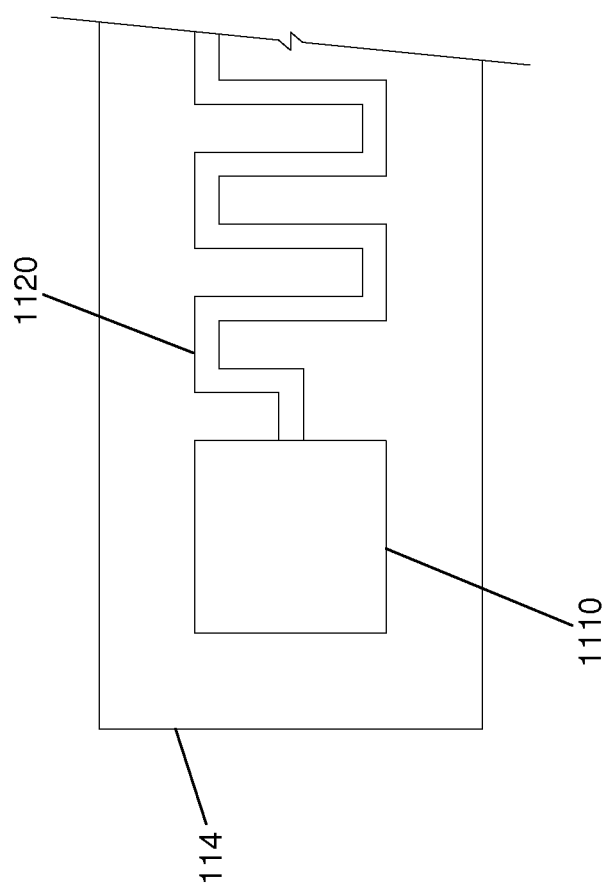
FIG. 11 is an illustration of a portion of an example cartridge that can be used to hold discarded products of a sample test.

Referring again to FIG. 2, method 200 may include the step of discarding a sample 500. Example procedures for discarding portions of a sample 500 (i.e., unreacted testing sample and rinsing fluid) may include discarding the portion of the sample 500 within a portion of a cartridge 114. FIG. 11 illustrates an example embodiment cartridge 114, which can include a discard reservoir 1110 to accept discarded unreacted testing sample and rinsing fluid via a flow channel 1120.

Figure 12:
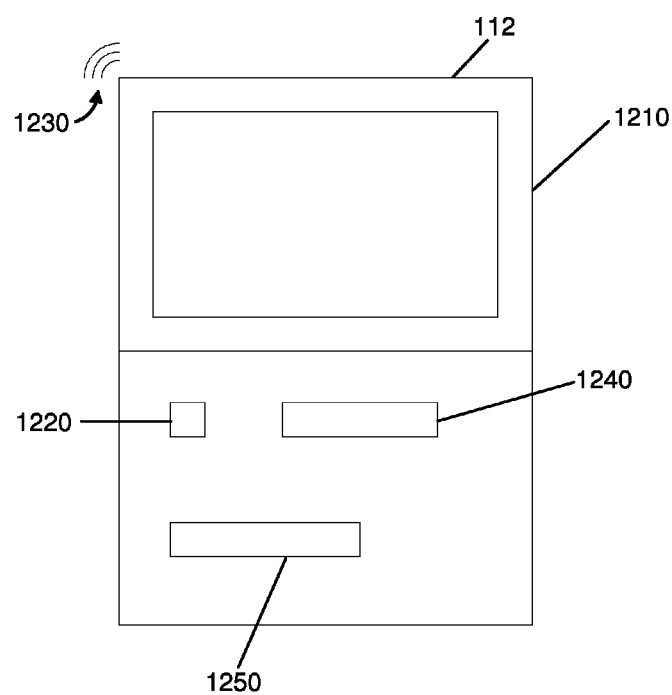
FIG. 12 is an illustration of example outputs that may be provided by an example diagnostic system.

Method 200 may include the step of outputting results 600. Example procedures for outputting results 600 may include gathering the processing sample results from step 400 and outputting the results via the diagnostic instrument 112. FIG. 12 illustrates an example diagnostic instrument, which can include various devices for outputting the results. As illustrated in FIG. 12, the diagnostic instrument 112 may include a display panel 1210 for displaying results, a port 1220 for connection to external media, such as a Universal Serial Bus (USB) port, a firewire port, etc., a wired or wireless electronic connection 1230 to transmit results via electronically to another location, such as a wireless internet transmitter, an Ethernet cable, etc., a print device 1240 to print out the results, such as a printer, or a media writing device 1250 to create a media format, such as a Compact Disk (CD).

G. Embodiments

Figure 13:
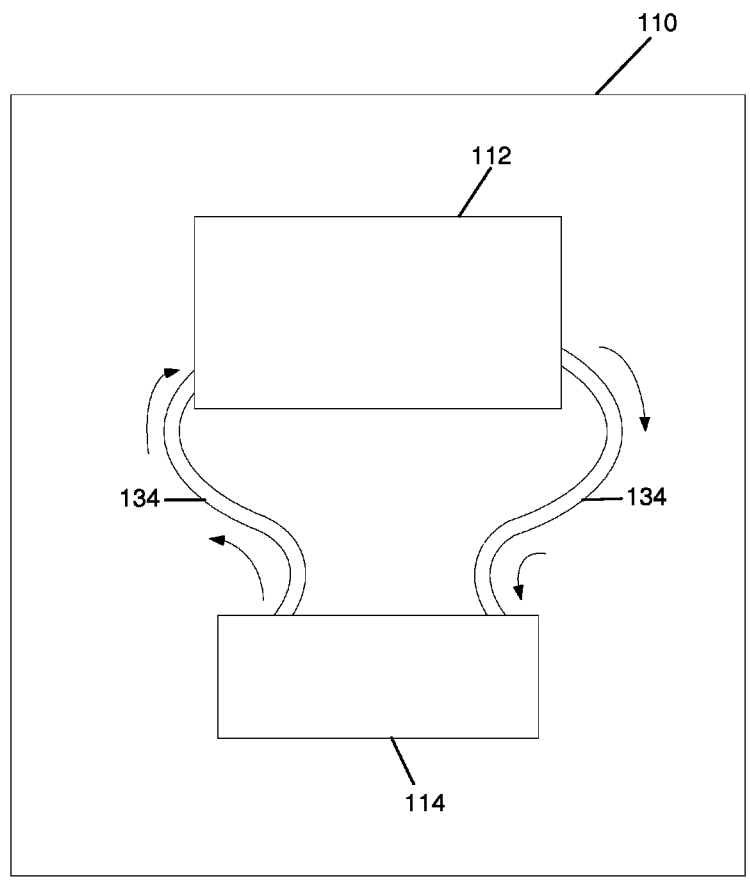
FIG. 13 is an illustration of a fluidic pathway between an example instrument and an example cartridge of an example diagnostic system.

FIG. 13 is an illustration of a diagnostic system 110 having a diagnostic instrument 112 fluidically connected to a cartridge 114 by way of fluidic pathways 134. The arrows indicate an example of a substantially single direction of flow for the materials travelling through the diagnostic system 110. In some embodiments, the disposal of processed materials can be returned to the cartridge without cross-contamination between tests run on the diagnostic instrument due to a substantially single direction of flow that the fluids in the diagnostic test follow.

The diagnostic system 110 can include a cartridge 114 that is self-contained and compact. Various embodiments of the diagnostic system 110 contemplate that a sample can be introduced into a cartridge 114 where it can be processed within the cartridge 114 during a diagnostic test. The cartridge 114 can be introduced into a diagnostic instrument 112 having the mechanical and electrical components necessary to run the diagnostic test and detect results using detection technology contained within the diagnostic instrument 112. The components and methods associated with the cartridge 114 will be described in more detail in the following disclosure.

The cartridge 114 can be configured to perform the steps of a diagnostic test completely within the diagnostic system 110 in conjunction with a diagnostic instrument 112 of the diagnostic system 110. For example, the cartridge 114 can store and hold all necessary reagents and materials necessary to perform a particular diagnostic test, such as an assay. The cartridge 114 can also be configured to store the reagents and materials in separate compartments, and provide air-tight and liquid-tight seals that can assist in diagnostic test functions, which will be described in further detail in the following disclosure.

The cartridge 114 can also be configured to receive a biological sample for processing and analysis during the diagnostic test. Through cooperative mechanisms with the diagnostic instrument 112, the biological sample can be prepared and processed completely within the diagnostic system 110 without the requirement for end-user input, once the sample is collected and introduced into the cartridge 114. The cooperative mechanisms between the cartridge and the diagnostic instrument of the diagnostic system also will be described in further detail in the following disclosure.

The cartridge 114 can also be configured to retain and collect substantially all of the processed sample, reagents, and materials used in the diagnostic test for disposal once the diagnostic test is completed. This not only provides added convenience of being self-contained but it also prevents and/or reduces cross-over or contamination between different diagnostic tests run on the same diagnostic instrument. The mechanisms involved in collecting the used materials also will be described in further detail in the following disclosure.

Examples of certain embodiments of a cartridge 114 are disclosed in co-pending U.S. Design application Ser. Nos. 29/420,961 and 29/420,967, both filed on May 15, 2012, and each of which is herein incorporated by reference in its entirety. Images contained within those disclosures prescribe exemplary diagnostic cartridges of the diagnostic system, and designs thereof, which relay both the function and form, and the connection between the product, the user, and the environment. Such images merely represent exemplary cartridges, diagnostic systems, and the present disclosure is not limited to these particular designs.

Figure 14A:
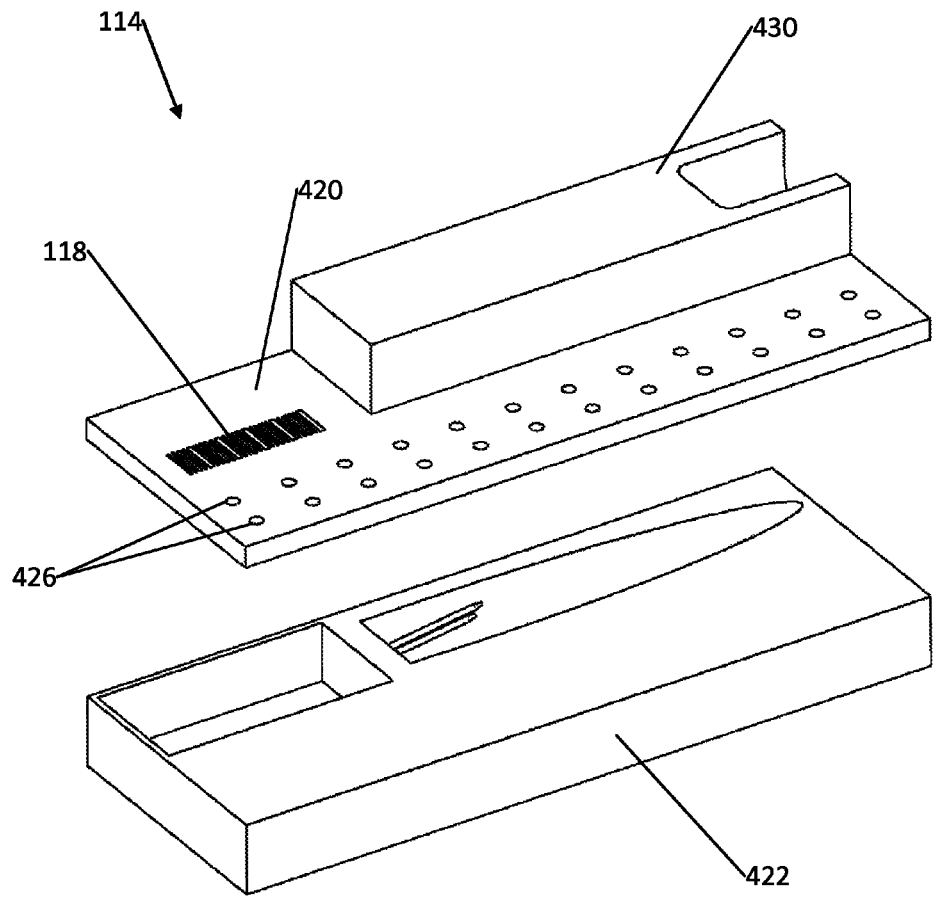
FIG. 14A is an illustration of an exploded perspective view of an example body and a cover of a cartridge of a diagnostic system.

FIG. 14A illustrates a perspective view of a body and a cover of a cartridge 114 of a diagnostic system 110. Various embodiments of a cartridge 114 contemplate having a cover 420 and a body 422 that mate together to form the cartridge 114.

Figure 14B:
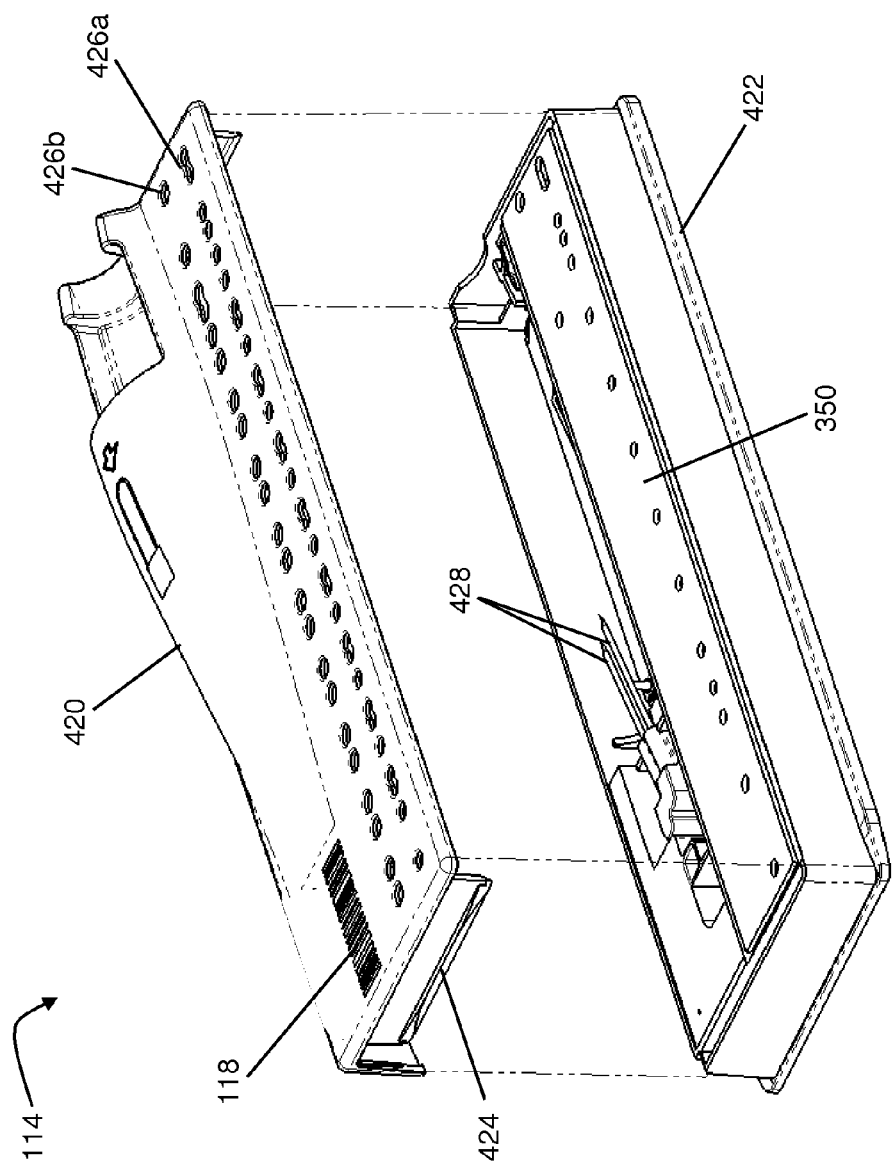
FIG. 14B is an illustration of an exploded perspective view of an example cartridge of a diagnostic system.

FIG. 14B illustrates a perspective view of an example of an embodiment of a cartridge 114 of a diagnostic system 110. The cover 420 can have at least one retaining feature 424 to facilitate connecting the cover 420 to the body 422. For example, the at least one retaining feature 424 can include a snap fit on one or both ends of the cover 420.

Figure 15A:
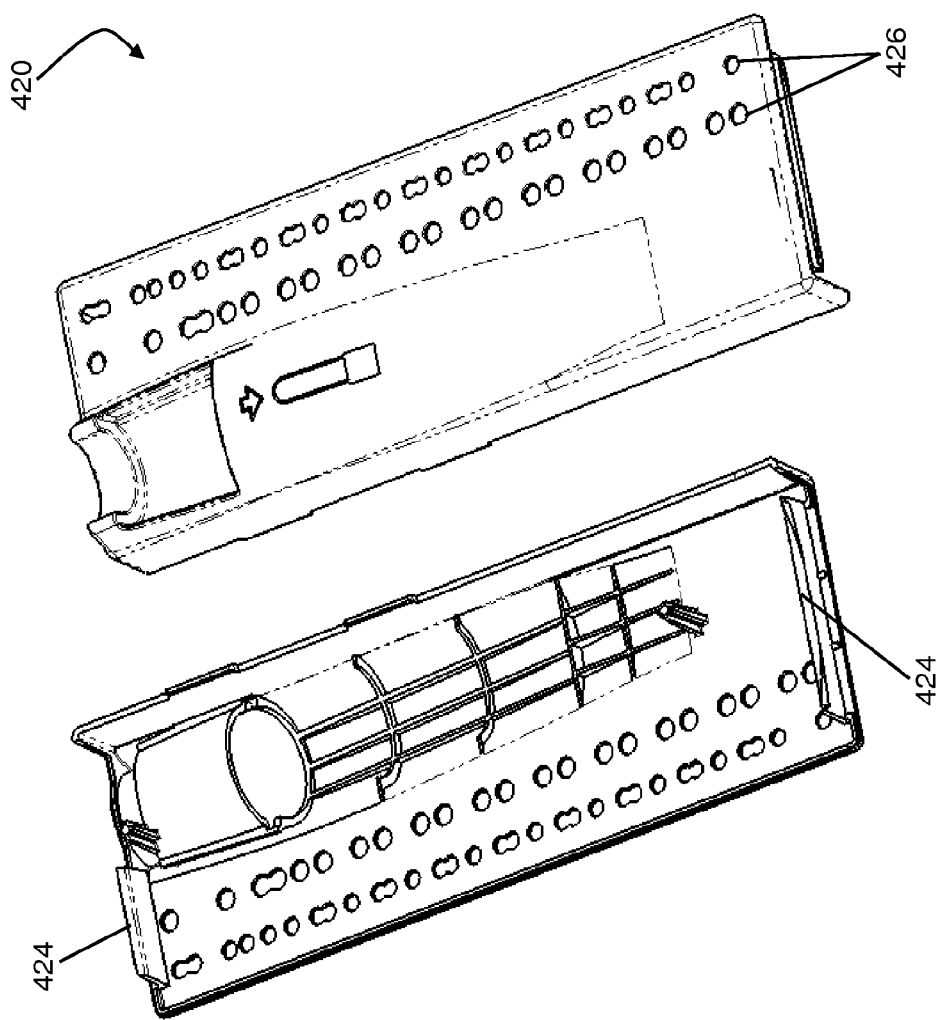
FIG. 15A is an illustration of a perspective view of an example of the front and back of a cartridge cover of a diagnostic system.
Figure 15B:
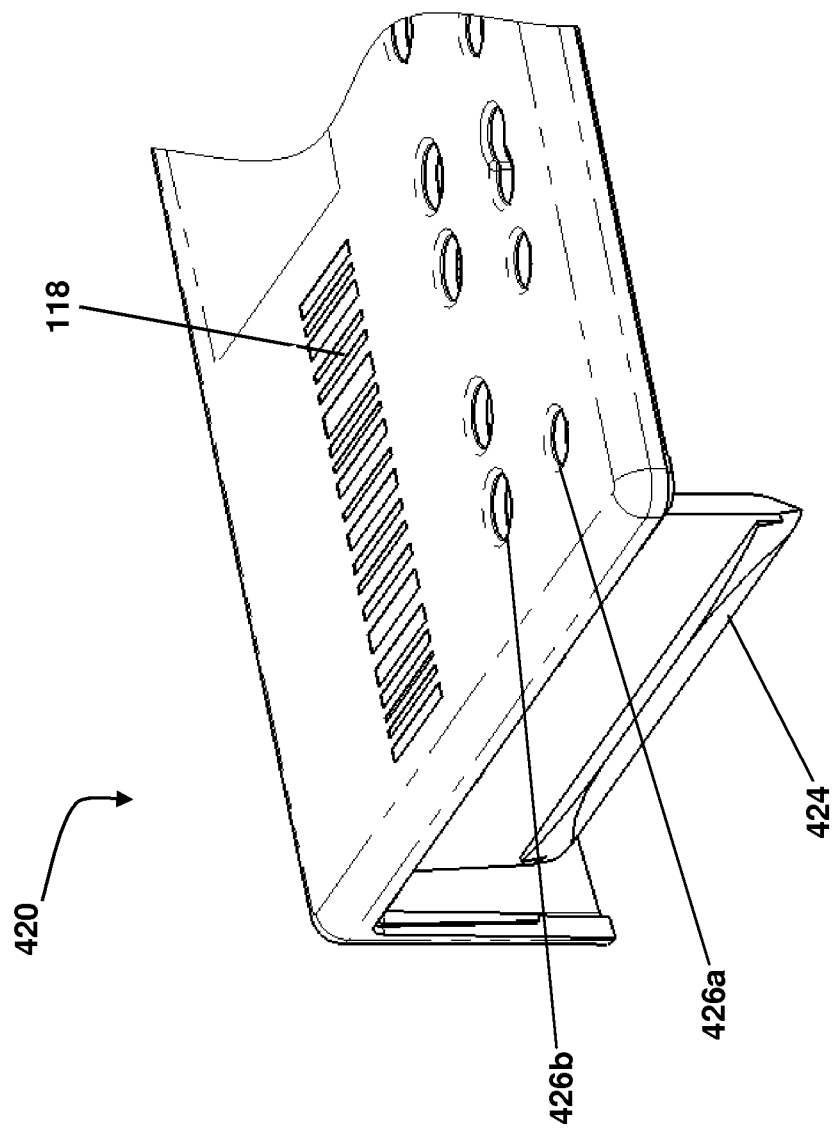
FIG. 15B is an illustration of a perspective view of an example of a portion of a cartridge cover of a diagnostic system.

FIGS. 15A and 15B illustrate the at least one retaining feature 424, and also show the examples of a cover 420, which can have a pull on each end of the cover 420 to ensure a secure fit to the body 422. It is contemplated that additional retaining features known in the art can be designed and included in the cover 420 to assist in securing the cover 420 to the body 422, including, but not limited to, press fits, tabs, spring locks, and over-molded magnets.

Various embodiments of the cartridge 114 contemplate that the cover 420 can have a flat area which makes contact with and covers the body 422, effectively covering and protecting the components of the body 422. No liquid or air tight seals are needed between the cover 420 and the rest of the cartridge 114. An optical machine-readable label 118 can be positioned on a portion of the flat area of the cover 420 for identification as previously discussed and as part of one of many failsafe mechanisms incorporated into the diagnostic system 110.

The cover 420 may also make the cartridge 114 as a whole look more aesthetically pleasing. The cover 420 can be injected molded out of a variety of sturdy materials, such as, poly(methyl methacrylate) (PMMA), polycarbonate (PC), polycarbonate/Acrylonitrile butadiene styrene (PC/ABS) blends. It is contemplated that other materials may be used to form the cover 420 depending on desired specifications and manufacturing goals for the disposable cartridge 114, such as, for example, a polycarbonate/acrylonitrile butadiene styrene such as GE Cycoloy HC 1204HF, a polycarbonate such as Sabic Lexan (PC) EXL9134, polyethylene terephthalate (PET), polypropylene (PP), polyvinyl chloride (PVC), and Teflon. It is contemplated that other known methods of forming the cover 420 can be employed, including, but not limited to casting, rotational molding, thermoforming, compression molding, and injection molding.

With reference to FIG. 14B, functionally, the cover 420 can assist in guiding a sample holder (not shown), such as a commercially available VACUTAINER® sample holder, onto at least one needle 428 integrated into the body 422 and used during processing of a diagnostic test. The cover 420 also serves to protect an operator from the sharp point of the at least one needle 428.

Various embodiments of the cartridge 114 contemplate having structural and functional features useful for filtration of a sample, assay processing regions (each region also referred to as a cartridge assay replicate or CAR), probe wash areas and draw reservoirs filled with ECL read buffer (can also be referred to as a read buffer filled reagent handling station (RHS)), and a pump storage fluid filled RHS. Certain embodiments contemplate that some components of the cartridge 114 can be attached to the body 422, including, for example, the cover 420, a filtration module 330, at least one needle 428, and multiple seals.

The cartridge 114 may include a sample holder mount. Various embodiments of a cartridge 114 contemplate having a sample holder mount 430 and having a sample holder 116. For example, the body 422 can be configured to accommodate the mounting of an industry standard sample holder (i.e., VACUTAINER®), or similar sample holder 116, which can connect to a fluidic pathway of the diagnostic system 110. As previously described, the sample can be a biological sample such as blood, plasma, urine or sputum.

In certain embodiments, the sample holder mount 430 can be configured to guide a sample holder 116 onto at least one needle 428 to establish fluidic communication, such as, for example, with a diagnostic instrument 112. The guide features 434 can also facilitate the piercing of the desired portion of the sample holder's septum 438 by physically constraining the radial motion of the sample holder 116. The at least one needle 428 can be mounted on the framework 432 to facilitate its insertion into the septum 438 of a sample holder 116, which would thereby facilitate, establish and maintain the fluidic connections between the at least one needle 428 and a diagnostic instrument 112.

Various embodiments of the diagnostic system 110 contemplate having a filtration module 530, such as that previously described in method 400 and depicted in FIG. 5, in fluidic communication with the sample holder 116 and a cartridge 114. Various embodiments of the diagnostic system 110 also contemplate a method of filtering a sample with the filtration module 530 within a cartridge 114. Examples of suitable filtration modules and methods of filtration are described in the '253 application and the '041 PCT application. The filtration module 530 can be designed such that it maintains the compact size and self-contained nature of the cartridge 114.

Figure 16:
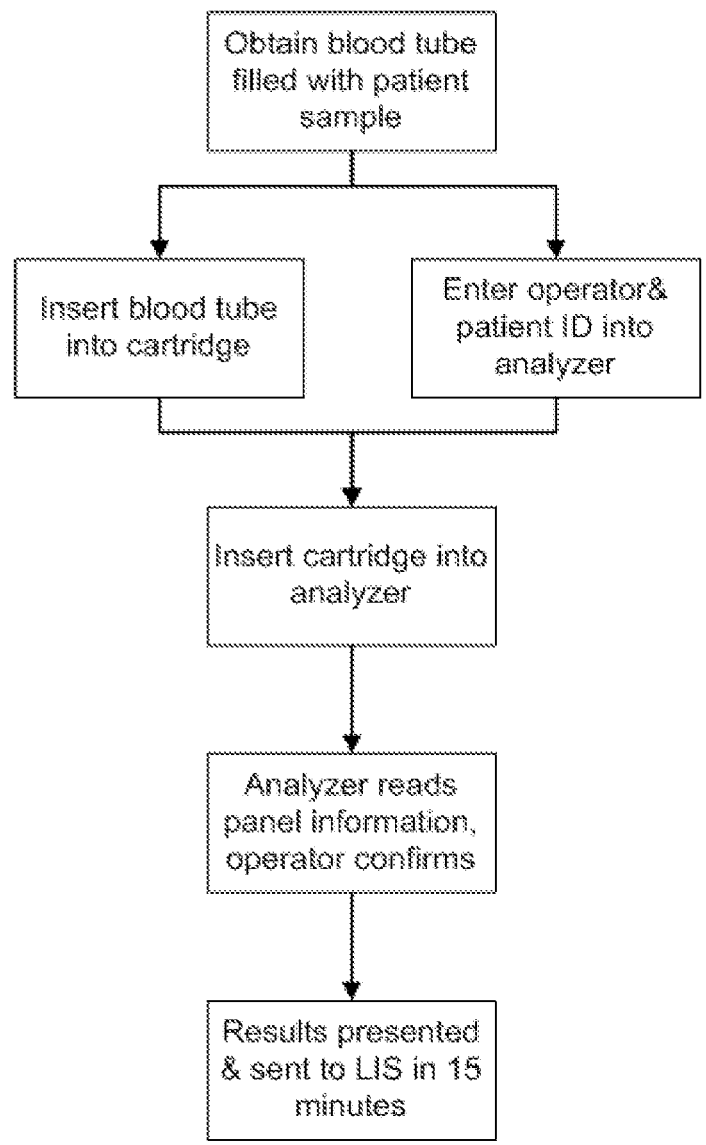
FIG. 16 is a flow chart for an example instrument-driven work flow.

FIG. 16 is an illustration of a flow chart for an example instrument-driven work flow. A user or operator can draw blood into a blood tube using standard practices. In the instrument-driven mode, the user or operator (in either order) can insert the blood tube into the cartridge and can enter the patient ID and operator ID into the diagnostic instrument. The diagnostic instrument, after reading the panel information from the cartridge, may ask the operator to confirm the panel. The user or operator can insert the cartridge into the diagnostic instrument. The diagnostic instrument or analyzer, after reading the panel information from the cartridge, may ask the user to confirm the panel. Afterwards, the sample is processed and results are presented, for example, in roughly 15 minutes.

Figure 17:
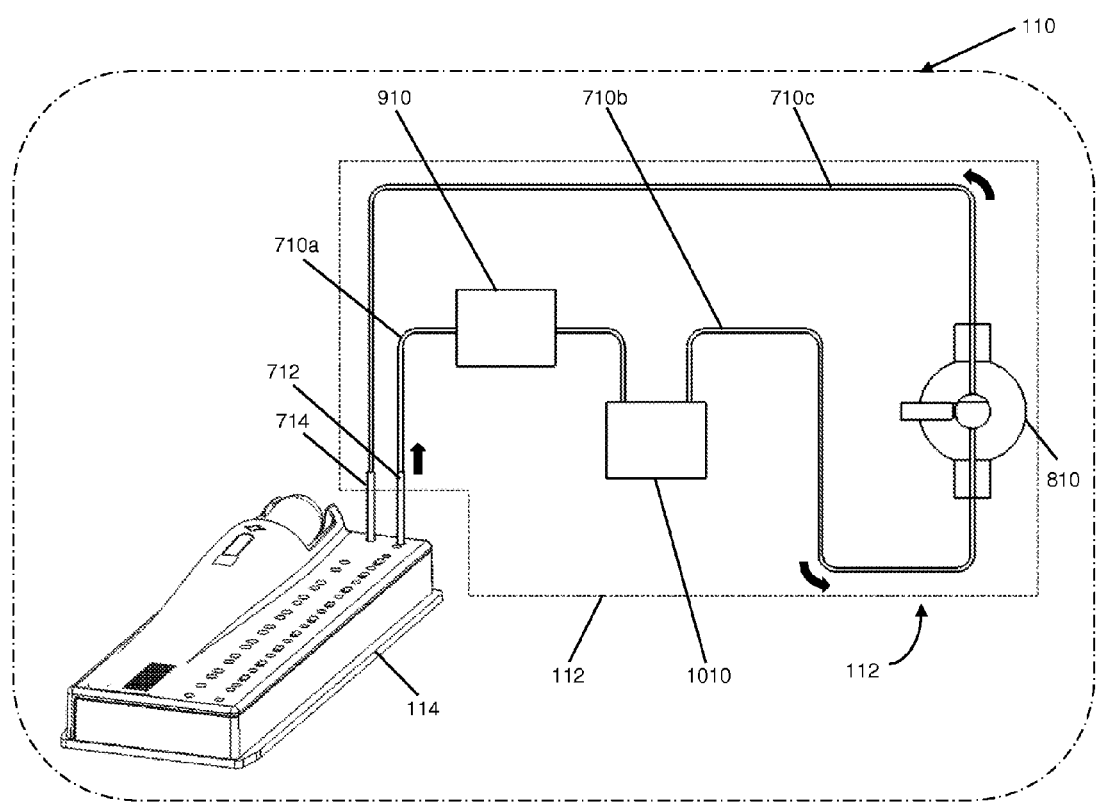
FIG. 17 is an overview illustration of an example closed fluidic path between a diagnostic instrument and a cartridge.

FIG. 17 is an overview illustration of a closed fluidic path 710 (see, e.g., 710a, 710b, 710c) between a diagnostic instrument 112 and a cartridge 114 of a diagnostic system 110. Various embodiments of a diagnostic instrument 112 contemplate having mechanical and electrical components that are connected fluidically to a cartridge 114 by a closed fluidic path 710. For example, the closed fluidic path 710 can fluidically connect a cartridge 114 via a first probe 712 to optional features along the closed fluidic path 710, such as a non-ECL detection module 910 via path 710a, at least one ECL detection apparatus 1010, a pump 810 via path 710b and returning to the cartridge 114 via path 710c and a second probe 714. The closed fluidic path 710 provides a pathway through which diagnostic materials, such as a biological sample and dry and liquid reagents, can be withdrawn from the cartridge 114, and can travel through the diagnostic instrument 112. After processing, the processed reagents and other waste materials can be returned to the cartridge 114 using a substantially single direction of flow (indicated by arrows).

Figure 18:
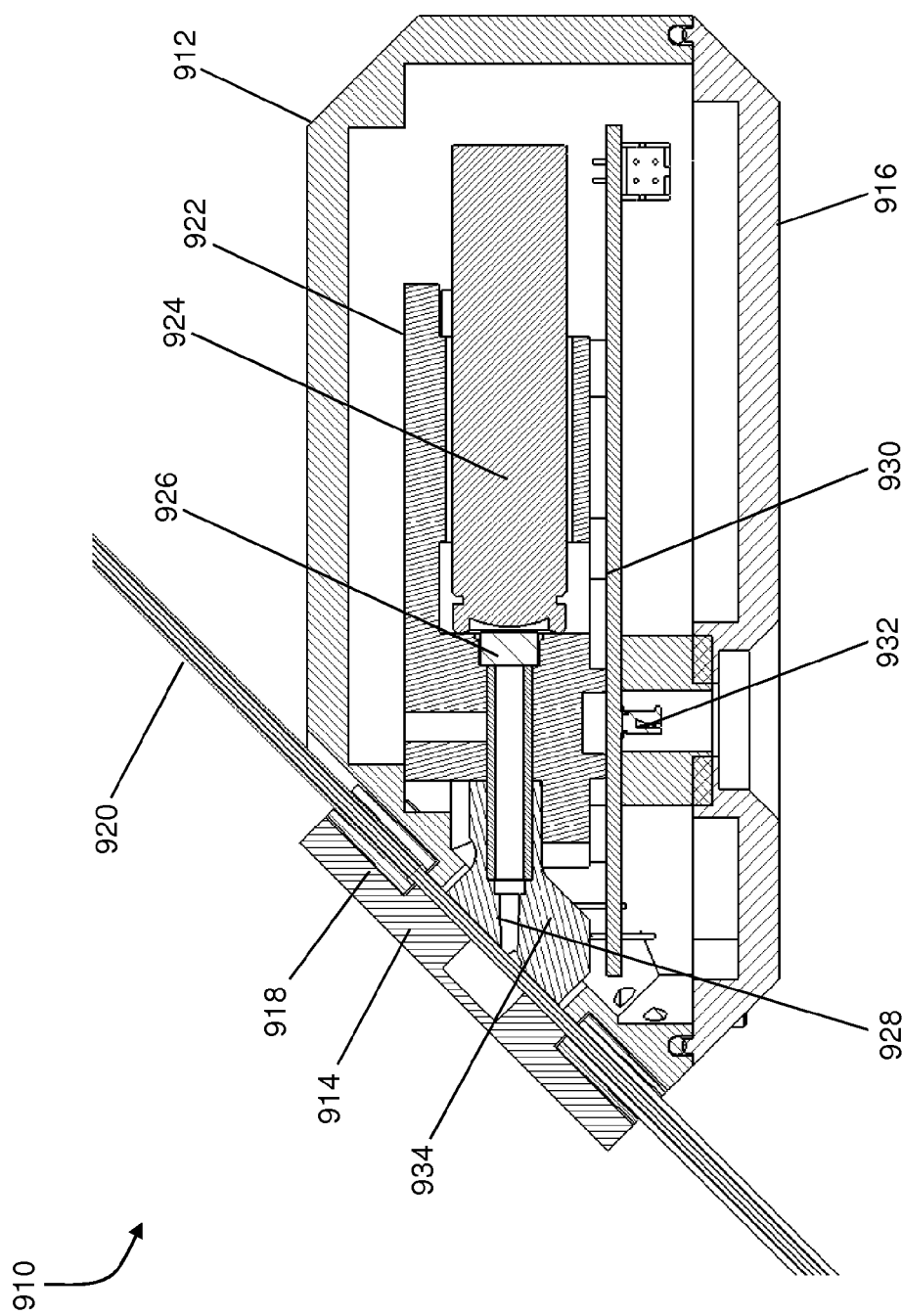
FIG. 18 is an illustration of an example of an internal standard (IS), non-ECL detection apparatus.

FIG. 18 is an illustration of an example of an internal standard (IS), non-ECL detection apparatus 910 that can be provided. Various embodiments of the diagnostic system 110 can contemplate a non-ECL detection apparatus 910 for use as a failsafe mechanism to ensure the precise and accurate function of the diagnostic system 110. In some embodiments, one such failsafe mechanism can include an internal standard (IS) non-ECL detection apparatus 910 to the diagnostic system 110. An IS can be a substance that can be added in a constant quantity to samples and calibration standards in an assay or analysis. An IS can be a substance that is very similar, but not identical to the substance of interest in the sample. The effects of assay construction should be the same for the IS as the substance of interest.

The non-ECL detection apparatus 910 can include a housing 912 with a tubing assembly 920 within the housing 912 that can carry a sample to be analyzed. As the sample passes through the housing 912, a laser 924 can be directed through a filter 926 and the laser light can be reflected through the sample. The reflected light can be used to detect the presence of a particular analyte within the sample as it flows through the non-ECL detection apparatus 910. For example, an IS can be used within the detection analysis.

One purpose of an IS can be to identify failures that might occur during assay construction. As such, a method to implement the IS operates as a failsafe mechanism. Another purpose of an IS to correct for normal variability in assay construction. As such, the method to implement the IS operates as a means to improve precision and accuracy. Further discussion about ISs and failsafe mechanisms can be found in related International PCT application no. PCT/US2013/041252, filed on May 15, 2013, entitled "CLINICAL DIAGNOSTIC SYSTEMS INCLUDING INSTRUMENT AND CARTRIDGE," and its US national stage application, filed on Nov. 14, 2014, having U.S. application Ser. No. 14/401,275, each of which was incorporated by reference.

While the invention has been described in detail with reference to preferred embodiments thereof, it will be apparent to those skilled in the art that variations and modifications can be made, and equivalents employed without departing from the scope of the appended claims.

What is claimed is:

1. A diagnostic system, comprising:
an instrument comprising an electrochemiluminescence (ECL) detector; and
a cartridge configured to fit within a portion of the instrument, wherein the cartridge comprises:
at least one reagent including an ECL label;
a blood collection holder;
at least one blood collection holder needle;
a blood collection holder structure; and
a closed fluidic path between the blood collection holder and the instrument; wherein the closed fluidic path provides the at least one reagent from the cartridge to the instrument, and then provides the at least one reagent from the instrument to the cartridge.

2. The diagnostic system of claim 1, wherein the instrument further comprises a pump, an incubator, a sensor, a magnet, and an output device.

3. The diagnostic system of claim 1, wherein the cartridge further comprises a filter or a discard reservoir,
wherein the filter, if present, filters plasma from whole blood, and
wherein the discard reservoir, if present, gathers the at least one reagent including the ECL label and contents from the blood collection holder.

4. The diagnostic system of claim 1, wherein the blood collection holder comprises a blood collection tube.

5. A system, comprising:
a diagnostic instrument comprising:
a pump;
an electrochemiluminescence (ECL) detector;
an incubator;
a magnet; and
an output device; and
a cartridge configured to fit within a portion of the diagnostic instrument;
a sample holder configured to fit within the cartridge; and
a closed fluidic path between the diagnostic instrument and the cartridge when the cartridge is fit within a portion of the diagnostic instrument, wherein the cartridge is configured to accept a sample from the sample holder and place the sample in fluidic communication with the diagnostic instrument via the closed fluidic path,
wherein the ECL detector comprises:
at least two electrodes; and
a gasket, wherein the gasket separates the at least two electrodes, and wherein a measurement containment area is formed by the gasket and the at least two electrodes, and wherein the ECL detector measures ECL labels within the measurement containment area.

6. The system of claim 5,
wherein the gasket maintains a predetermined spacing between the at least two electrodes to form the measurement containment area, and
wherein the gasket comprises an elastomeric material.

7. The system of claim 5, wherein the incubator comprises:
one or more sensors; and
one or more heating and/or cooling elements, wherein the one or more sensors and the one or more heating and/or cooling elements provide a predetermined temperature to a portion of the closed fluidic channel within the cartridge.

8. The system of claim 5, wherein the cartridge further comprises:
at least one sample holder needle; and
a sample holder structure, wherein the sample holder fits within the sample holder structure and the sample is accessible to the closed fluidic path via the at least one sample holder needle.

9. The system of claim 5, wherein the cartridge further comprises a filter within the closed fluidic path, wherein the filter is configured to separate portions of the sample.

10. The system of claim 5, wherein the cartridge further comprises a discard reservoir within the closed fluidic path, wherein the discard reservoir is configured to hold contents of the closed fluidic path, and wherein the system is a self-contained diagnostic system.

11. A method of providing Point of Care (POC) services, comprising:
providing a biological sample;
introducing the biological sample to a cartridge;
providing the cartridge to a diagnostic instrument comprising an electrochemiluminescence (ECL) detector;
mixing the biological sample with a reagent in the cartridge to form a biological sample-reagent mixture;
providing at least a portion of the biological sample-reagent mixture from the cartridge to the diagnostic instrument in a closed fluidic path;
analyzing the biological sample-reagent mixture using the ECL detector;
outputting the results from the analyzing step; and
providing at least a portion of the biological sample-reagent mixture from the diagnostic instrument to the cartridge in the closed fluidic path.

12. The method of claim 11, wherein the introducing the biological sample to a cartridge comprises:
inserting a blood collection holder containing the biological sample into a preconfigured area of the cartridge; and
allowing the biological sample from the blood collection holder to be available to fluidic channels within the cartridge.

13. The method of claim 12, wherein the inserting of the blood collection holder into the preconfigured area of the cartridge comprises inserting the blood collection holder into a blood collection holder mount that includes at least one blood collection needle that allows the biological sample to be available to fluidic channels within the cartridge.

14. The method of claim 11, wherein the providing the cartridge to a diagnostic instrument comprising an ECL detector comprises:
fitting the cartridge into a preconfigured area of the diagnostic instrument, wherein the preconfigured area of the diagnostic instrument is a slot in the diagnostic instrument shaped specifically for the cartridge.

15. The method of claim 11, wherein the mixing the biological sample with a reagent in the cartridge to form a biological sample-reagent mixture comprises:
mixing the biological sample with the reagent, wherein mixing moves the biological sample together with the reagent within a fluidic channel to form detectable complexes in the biological sample-reagent mixture.

16. The method of claim 11, wherein the analyzing the biological sample-reagent mixture using the ECL detector comprises:
introducing the biological sample-reagent mixture into the ECL detector;
applying a light source to the biological sample-reagent mixture within a measurement containment area of the ECL detector; and
detecting the number of ECL labels within the biological sample-reagent mixture using the ECL detector.

17. The method of claim 11, wherein the outputting the results from the analyzing step comprises:
gathering results from the analyzing step; and
outputting results to the diagnostic instrument to supply a user with the results.

18. The method of claim 11, further comprising filtering the biological sample by:
flowing the biological sample through a filtration module within the cartridge to divide the biological sample into a testing sample and a waste product.

19. The method of claim 18, wherein the flowing of the biological sample through a filtration module comprises flowing the biological sample through one or more filtration layers.

20. The method of claim 18, wherein the providing at least a portion of the biological sample-reagent mixture from the diagnostic instrument to the cartridge comprises collecting the testing sample in a testing sample cache within the cartridge.

21. The method of claim 18, wherein the providing at least a portion of the biological sample-reagent mixture from the diagnostic instrument to the cartridge comprises collecting the waste product in a waste product collector within the cartridge.

22. The method of claim 11, further comprising incubating the biological sample-reagent mixture by:
heating and/or cooling with one or more heating and/or cooling elements the biological sample-reagent mixture;
sensing with one or more sensors a temperature of the biological sample-reagent mixture; and
adjusting a temperature of the incubator to a predetermined temperature.

23. The method of claim 11, further comprising washing the biological sample-reagent mixture by:
positioning the biological sample-reagent mixture within a portion of the cartridge within an electromagnetic field of a magnet of the diagnostic instrument;
magnetically attracting a first portion of the biological sample-reagent mixture to the magnet; and
washing away a second portion of the biological sample-reagent mixture with a rinsing fluid to expose the detectable complex for analyzing.

24. The method of claim 11, further comprising analyzing the biological sample-reagent mixture using an internal standard (IS) detector.

25. The method of claim 24, further comprising providing a failsafe mechanism by comparing results from the analyzing of the biological sample-reagent mixture by the IS detector with results from the analyzing of the biological sample-reagent mixture by the ECL detector.

* * * * *